US009642805B2

(12) United States Patent  
Odom et al.

(10) Patent No.: US 9,642,805 B2
(45) Date of Patent: May 9, 2017

(54) APTAMER-LOADED, BIOCOMPATIBLE NANOCONSTRUCTS FOR NUCLEAR-TARGETED CANCER THERAPY

(71) Applicant: Northwestern University, Evanston, IL (US)

(72) Inventors: Teri W. Odom, Chicago, IL (US); Duncan-Hieu M. Dam, Chicago, IL (US); Jung Heon Lee, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 13/671,347

(22) Filed: Nov. 7, 2012

(65) Prior Publication Data

US 2013/0115254 A1 May 9, 2013

Related U.S. Application Data

(60) Provisional application No. 61/556,663, filed on Nov. 7, 2011, provisional application No. 61/560,113, filed on Nov. 15, 2011.

(51) Int. Cl.
| | |
|---|---|
| *C12N 15/11* | (2006.01) |
| *A61K 9/14* | (2006.01) |
| *A61K 31/711* | (2006.01) |
| *A61K 41/00* | (2006.01) |
| *A61K 47/48* | (2006.01) |
| *B82Y 5/00* | (2011.01) |

(52) U.S. Cl.
CPC .............. *A61K 9/14* (2013.01); *A61K 31/711* (2013.01); *A61K 41/0042* (2013.01); *A61K 47/48861* (2013.01); *B82Y 5/00* (2013.01); *Y10S 977/773* (2013.01); *Y10S 977/906* (2013.01)

(58) Field of Classification Search
CPC .......................... C12N 15/115; C12N 2310/16
See application file for complete search history.

(56) References Cited

U.S. PATENT DOCUMENTS

| 6,867,289 B1* | 3/2005 | Gorenstein ............ C07H 21/00 530/350 |
| 2008/0160090 A1* | 7/2008 | Oraevsky et al. ............ 424/489 |
| 2010/0061974 A1* | 3/2010 | Quadros et al. ............ 424/130.1 |
| 2012/0107242 A1* | 5/2012 | Wang et al. ................. 424/9.1 |
| 2013/0095039 A1* | 4/2013 | Lu et al. ..................... 424/9.1 |

FOREIGN PATENT DOCUMENTS

WO        2011049750        4/2011

OTHER PUBLICATIONS

Soundararajan et al. (Molecular Pharmacology 76:984-991, 2009).*
Kang et al. American Chemical Society, 5, 5094-5099, 2011.*
Yavuz et al. Nat. Mater. 2009, 8:935-939.*
Wijaya et al. (ACS, 3, 2009, pp. 80-86).*
Hasegawa et al. Sensors 2008, 8, 1090-1098.*
Kang, B.; MacKey, M.A.; El-Sayed, M.A. Nuclear Targeting of Gold Nanoparticles in Cancer Cells Induces DNA Damage, Causing Cytokinesis Arrest and Apoptosis. J. Am. Chem. Soc. 2010, 132, pp. 1517-1519.
Tkachenko, A.G.; Xie, H.; Coleman, D.; Glomm, W.; Ryan, J.; Anderson, M.F.; Franzen, S.; Feldheim, D.L. Multifunctional Gold Nanoparticle—Peptide Complexes for Nuclear Targeting. J. Am. Chem. Soc. 2003, 125, pp. 4700-4701.
Sun, L.; Liu, D.; Wang, Z. Functional Gold Nanoparticle—Peptide Complexes as Cell-Targeting Agents. Langmuir 2008, 24, pp. 10293-10297.
Oyelerer, A.K.; Chen, P.C.; Huang, X.; El-Sayed, I.H.; El-Sayed, M.A. Peptide-Conjugated Gold Nanorods for Nuclear Targeting. Bioconjugate Chem. 2007, 18, pp. 1490-1497.
Dam, H.M.; Lee, J.H;. Sisco, P.N.; Co, D.T.; Zhang, M.;. Wasielewski, M.R.; Odom, T.W. Direct Observation of Nanoparticle—Cancer Cell Nucleus Interactions. ACSNANO, vol. 6, No. 4. pp. 3318-3326, 2012. Published online Mar. 16, 2012.
International Search Report dated Mar. 13, 2013.
Anger, P. et al., "Enhancement and Quenching of Single-Molecule Fluorescence", Phys Rev Lett, 96, 113002, 2006.
Ashkenazi, A., "Targeting Death and Decoy Receptors of the Tumour-Necrosis Factor Superfamily", Nat Rev Cancer, 2, 420-430, 2002.
Bates, P. J. et al., "G-Rich Oligonucleotides for Cancer Treatment", Methods Mol Biol, 542, 379-392, 2009.
Bates, P.J. et al., "Discovery and development of the G-rich oligonucleotide AS1411 as a novel treatment for cancer", Experimental and Molecular Pathology, 86, 151-164, 2009.
Bertoletti, A. et al., "The immune response during hepatitis B virus infection", J Gen Virol, 87, 1439-1449, 2006.
Borer, R.A. et al, "Major Nucelolar Proteins Shuttle between Nucleus and Cytoplasm", Cell, 56, 379-390, 1989.
Brannon-Peppas, L. et al., "Nanoparticle and targeted systems for cancer therapy", Adv Drug Deliver Rev, 56, 1649-1659, 2004.
Brown, K. C., "New approaches for cell-specific targeting: identification of cellselective peptides from combinatorial libraries", Current opinion in chemical biology, 4, 16-21, 2000.
Cao, Z. et al., "Reversible Cell-Specific Drug Delivery with Aptamer-Functionalized Liposomes", Angew Chem Int Ed Engl, 48, 6494-6498, 2009.
Chen, X. et al., "Cell Surface Nucleolin Serves as Receptor for DNA Nanoparticles Composed of Pegylated Polylysine and DNA", Molecular Therapy, 16, 333-342, 2008.
Davis, M.E. et al., "Nanoparticle therapeutics: an emerging treatment modality for cancer", Nature Reviews Drug Discovery, 7, 771-782, 2008.
De la Fuente, J.M. et al., Tat Peptide as an Efficient Molecule to Translocate Gold Nanoparticles into the Cell Nucleus, Bioconjugate Chem, 16, 1176-1180, 2005.
Demers, L.M. et al., A Fluorescence-Based Method for Determining the Surface Coverage and Hybridization Efficiency of Thiol-Capped Oligonucleotides Bound to Gold Thin Films and Nanoparticles, Analytical Chemistry, 72, 5535-5541, 2000.

(Continued)

*Primary Examiner* — Brian Whiteman
(74) *Attorney, Agent, or Firm* — Reinhart Boerner Van Deuren s.c.

(57) ABSTRACT

Disclosed herein is a nanoconstruct comprising an aptamer and a gold nanostar. The nanoconstruct can be used in a method of inducing changes to a nuclear phenotype of a cell comprising transporting the nanoconstruct to a nucleus of a cell, and releasing the aptamer from a surface of the gold nanostar into the nucleus of the cell to afford deformations or invaginations in the nuclear membrane, thereby inducing changes to the nuclear phenotype. The method can be used to treat certain hyperproliferative disorders such as cancer.

22 Claims, 21 Drawing Sheets

(56) References Cited

OTHER PUBLICATIONS

Dexter, D. L. et al., "Tumor Heterogeneity and Drug Resistance", J Clin Oncol, 4, 244-257, 1986.
Douglas, T. et al., "Viruses: Making Friends with Old Foes", Science, 312, 873-875, 2006.
Ei-Sayed, I. H. et al., "Plasmonic photothermal therapy (PPTT) using gold nanoparticles", Laser Med Sci, 23, 217-228, 2008.
Franzen, S. et al., "Multifunctional Gold Nanoparticle-Peptide Complexes for Nuclear Targeting", J Am Chem Soc, 125, 4700-4701, 2003.
Fricker, M. et al., "Interphase Nuclei of Many Mammalian Cell Types Contain Deep, Dynamic, Tubular Membrane-bound Invaginations of the Nuclear Envelope", J Cell Biol, 136, 531-544, 1997.
Ginisty, H. et al., "Structure and functions of nucleolin", Journal of Cell Science, 112, 761-772, 1999.
Gu, F.X. et al., "Targeted nanoparticles for cancer therapy", Nano Today, 2, 14-21, 2007.
Harris, M., "Monoclonal antibodies as therapeutic agents for cancer", Lancet Oncol, 5, 292-302, 2004.
Hill, H. D. et al., The Role Radius of Curvature Plays in Thiolated Oligonucleotide Loading on Gold Nanoparticles, Acs Nano, 3, 418-424, 2009.
Hovanessian, A. G. et al., "Surface Expressed Nucleolin Is Constantly Induced in Tumor Cells to Mediate Calcium-Dependent Ligand Internalization", Plos One, 5, 2010.
Ireson, C. R. et al., "Discovery and development of anticancer aptamers", Mol Cancer Ther, 5, 2957-2962, 2006.
Jain, P.K. et al., Ultrafast Cooling of Photoexcited Electrons in Gold Nanoparticle-Thiolated DNA Conjugates Involves the Dissociation of the Gold-Thiol Bond, J Am Chem Soc, 128, 2426-2433, 2006.
Kang, B. et al., "Nuclear Targeting of Gold Nanoparticles in Cancer Cells Induces DNA Damage, Causing Cytokinesis Arrest and Apoptosis", J Am Chem Soc, 132, 1517-1519, 2010.
Kay, M.A. et al., "Viral vectors for gene therapy: the art of turning infectious agents into vehicles of therapeutics", Nat Med, 7, 33-40, 2001.
Kim, B. Y. et al., "Nanomedicine", The New England journal of medicine, 363, 2434-43, 2010.
Lee, L.A. et al., "Adaptations of nanoscale viruses and other protein cages for medical applications", Nanomedicine, 2, 137-149, 2006.
Miller, D. M. et al., "Extended phase I study of AS1411 in renal and non-small cell lung cancers", Ann Oncol, 17, 147-148, 2006.
Monahan, P.E. et al., "Adeno-associated virus vectors for gene therapy: more pros than cons?", Mol Med Today, 6, 433-440, 2000.
Mongelard, F. et al., "Nucleolin: a multiFACeTed protein", Trends in Cell Biology, 17, 80-86, 2006.
Munley, M.T. et al., "Multimodality nuclear medicine imaging in three-dimensional radiation treatment planning for lung cancer: challenges and prospects", Lung Cancer, 23, 105-114, 1999.
Nahta, R. et al., "The HER-2-Targeting Antibodies Trastuzumab and Pertuzumab Synergistically Inhibit the Survival of Breast Cancer Cells", Cancer Res, 64, 2343-2346, 2004.
Nimjee, S.M., Aptamers: An Emerging Class of Therapeutics, Annu Rev Med, 56, 555-583. 2005.
Otake, Y. et al., "Overexpression of nucleolin in chronic lymphocytic leukemia cells induces stabilization of bcl2 mRNA", Blood, 109, 3069-3075, 2007.
Peer, D. et al., "Nanocarriers as an emerging platform for cancer therapy", Nat Nanotechnol, 2, 751-760, 2007.
Reyes-Reyes, E. M. et al., "A New Paradigm for Aptamer Therapeutic AS1411 Action: Uptake by Macropinocytosis and Its Stimulation by a Nucleolin-Dependent Mechanism", Cancer Res, 70, 8617-8629, 2010.
Rogakou, E.P. et al., "DNA Double-stranded Breaks Induce Histone H2AX Phosphorylation on Serine 139", J Biol Chem 273, 5858-5868, 1998.
Rosi, N.L. et al., "Oligonucleotide-Modified Gold Nanoparticles for Intracellular Gene Regulation", Science, 312, 1027-1030, 2006.
Schwartz, G.K. et al., "Targeting the Cell Cycle: A New Approach to Cancer Therapy", J Clin Oncol, 23, 9408-9421, 2005.
Sengupta, T. K. et al., "Identification of Nucleolin as an AU-rich Element Binding Protein Involved in bcl-2 mRNA Stabilization", J Biol Chem, 279, 10855-10863, 2004.
Shin, D.M. et al., "Therapeutic Nanoparticles for Drug Delivery in Cancer", Clin Cancer Res, 14, 1310-1316, 2008.
Shipitsin, M. et al., "Molecular Definition of Breast Tumor Heterogeneity", Cancer cell, 11, 259-73, 2007.
Soundararajan, S. et al., "The Nucleolin Targeting Aptamer AS1411 Destabilizes Bcl-2 Messenger RNA in Human Breast Cancer Cells", Cancer Research, 68, 2358-2365, 2008.
Srivastava, M. et al., "Molecular dissection of nucleolin's role in growth and cell proliferation: new insights", Faseb Journal, 13, 1911-1922, 1999.
Stuart, R. K. et al., "Randomized phase II trial of the nucleolin targeting aptamer AS1411 combined with high-dose cytarabine in relapsed/refractory acute myeloid leukemia (AML)", J Clin Oncol, 27, 2009.
Swanton, C., "Intratumor Heterogeneity: Evolution through Space and Time", Cancer Res, 72, 4875-82, 2012.
Technical Bulletin, "Apo-ONE Homogeneous Caspase-3/7 Assay", P. Corporation, Ed. (Promega Corporation, Madison, WI, 2009), pp. 8.
Torchilin, V.P., "Recent Approaches to Intracellular Delivery of Drugs and DNA and Organelle Targeting", Annu Rev Biomed Eng, 8, 343-375, 2006.
Kang, Huaizhi et al., "Near-Infrared Light-Responsive Core-Shell Nanogels for Targeted Drug Deliver", American Chemical Society, 5, 5094-5099, 2011.
Soundararajan, Sridharan et al., "Plasma Membrane Nucleolin is a Receptor for the Anticancer Aptamer AS1411 in MV4-11 Leukemia Cells", Molecular Pharmacology, 76, 984-991, 2009.
Tuteja, R. et al., "Nucleolin: A Multifunctional Major Nucleolar Phosphoprotein", Crit Rev Biochem Mol Biol, 33, 407-436, 1998.
Xie, J. P. et al., "Seedless, Surfactantless, High-Yield Synthesis of Branched Gold Nanocrystals in HEPES Buffer Solution", Chem Mater, 19, 2823-2830, 2007.
Zaidi, S.K. et al., "Nuclear microenvironments in biological control and cancer", Nat Rev Cancer, 7, 454-463. 2007.
Zink, D. et al., "Nuclear Structure in Cancer Cells", Nat Rev Cancer 4, 677-687, 2004.

\* cited by examiner

APTAMER-LOADED, BIOCOMPATIBLE NANOCONSTRUCTS FOR NUCLEAR-TARGETED CANCER THERAPY

This invention was made with government support under grant numbers DP1OD003899, U54 CA119341, CA060553 awarded by the National Institutes of Health; grant numbers DMR1121262, EEC0647560, CHE9810378 awarded by the National Science Foundation; and grant number NNA06CB93G awarded by the National Aeronautics Space Administration. The government has certain rights in the invention.

The present invention relates generally to interactions between drug-loaded nanoparticles and a cell nucleus. Specifically, the invention relates to a method of inducing changes in nuclear phenotype of a cell by shuttling drug-loaded nanoparticles directly to a cell nucleus, the changes in nuclear phenotype correlated with cell activity.

BACKGROUND OF THE INVENTION

The nucleus is the most important organelle in the proliferation, angiogenesis, and apoptosis of a cell (Zink, D. et al., 2004 *Nat Rev Cancer* 4, 677; Torchilin, V. P., 2006 *Annu Rev Biomed Eng* 8, 343). Controlling the functions of the nucleus in cancer cell growth and division has been the primary motivation for nuclear-targeted cancer therapy (Schwartz, G. K. et al., 2005 *J Clin Oncol* 23, 9408; Ashkenazi, A., 2002 *Nat Rev Cancer* 2, 420; Zaidi, S. K. et al., 2007 *Nat Rev Cancer* 7, 454; Munley, M. T. et al., 1999 *Lung Cancer* 23, 105). In conventional treatment, viral vectors are used for delivering drugs to cells (Lee, L. A. et al., 2006 *Nanomedicine* 2, 137; Douglas, T. et al., 2006 *Science* 312, 873). However, this approach results an immunogenic response in the hosts (Bertoletti, A. et al., 2006 *J Gen Virol* 87, 1439; Monahan, P. E. et al., 2000 *Mol Med Today* 6, 433; Kay, M. A. et al., 2001 *Nat Med* 7, 33). Over the past ten years, nanomaterials have offered a new type of delivery vehicle for targeted therapy because the drugs can be densely loaded on the nanocarrier, which simultaneously enhances the stability and pharmacokinetics of the molecules in vitro (Rosi, N. L. et al., 2006 *Science* 312, 1027). Although therapy using nanomaterials has started to be explored, most work has focused on only targeting surface receptors overexpressed on the plasma membranes to deliver drugs into the interior of the cancer cells (Davis, M. E. et al., 2008 *Nature Reviews Drug Discovery* 7, 771; Brannon-Peppas, L. et al., 2004 *Adv Drug Deliver Rev* 56, 1649; Gu, F. X. et al., 2007 *Nano Today* 2, 14; Shin, D. M. et al., 2008 *Clin Cancer Res* 14; El-Sayed, I. H. et al., 2008 *Laser Med Sci* 23, 217). Recently, nuclear targeting by peptide-modified gold nanoparticles has seen some success and shown improved anti-cancer efficacy (de la Fuente, J. M. et al., 2005 *Bioconjugate Chem* 16, 1176; Oyelere, A. K. et al., 2007 *Bioconjugate Chem* 18, 1490; Franzen, S. et al., 2003 *J Am Chem Soc* 125, 4700; Kang, B. et al., 2010 *J Am Chem Soc* 132, 1517). This therapeutic enhancement has been attributed to the interaction of the nanomaterials with the cancer cell nucleus. However, direct visualization of this interaction was not observed.

Both primary and metastatic tumors contain different subpopulations of cancer cells, i.e tumor heterogeneity (Dexter, D. L. et al., *J Clin Oncol* 1986, 4, 244-57; Shipitsin, M. et al., *Cancer cell* 2007, 11, 259-73; Swanton, C., *Cancer Res* 2012, 72, 4875-82). Tumor heterogeneity is one cause of drug resistance in cancer treatments. Current commercially available drugs rely on specific surface receptors of cancer cells, such as CD20 and epidermal growth factor, to increase therapeutic effects while reducing side effects in treated patients (Harris, M., *Lancet Oncol* 2004, 5, 292-302; Nahta, R. et al., *Cancer Res* 2004, 64, 2343-2346). One major issue of these treatments is that not all cancer cells in the same tumor express the target receptor. Hence, these treatments become cell-type dependent and frequently cannot eradicate the entire population of tumor cells (Brown, K. C., *Current opinion in chemical biology* 2000, 4, 16-21).

Nucleolin is one of the most abundant nucleolar phosphoproteins in the nucleus of a normal cell (Borer, R. A. et al, 1989 *Cell* 56, 379; Tuteja, R. et al., 1998 *Crit Rev Biochem Mol Biol* 33, 407; Ginisty, H. et al., 1999 *Journal of Cell Science* 112, 761). This protein is responsible for many cellular activities, including DNA transcription, cell proliferation, and cell growth (Srivastava, M. et al., 1999 *Faseb Journal* 13, 1911). In metastatic cancer cells and exponentially growing cells, nucleolin is overexpressed in the cytoplasm and translocated to the plasma membrane (Soundararajan, S. et al., 2008 *Cancer Research* 68, 2358; Soundararajan, S. et al., 2009 *Molecular Pharmacology* 76, 984; Hovanessian, A. G. et al., 2010 *Plos One* 5; Chen, X. et al., 2007 *Molecular Therapy* 16, 333; Ginisty, H. et al., 1999 *Journal of cell science*, 112, 761-772). Its trafficking ability has been implicated in transporting anti-cancer ligands from the cell surface to the nucleus. Thus, nucleolin has received attention for nuclear targeting-based therapeutics in conjunction with the single stranded DNA aptamer AS-1411 (26 mer, 7.8 kDa), which in its G-quadruplex homodimer form binds to nucleolin with high binding affinity ($K_d$ is pM to low nM) (Mongelard, F. et al., 2007 *Trends in Cell Biology* 17, 80; Nimjee, S. M., 2005 *Annu Rev Med* 56, 555; Bates, P. J. et al., 2009 *Experimental and Molecular Pathology* 86, 151; Cao, Z. et al., 2009 *Angew Chem Int Ed Engl* 48, 6494). Aptamers, generally, are oligonucleotides that bind to specific moieties and act as targeting molecules, similar to monoclonal antibodies (mAbs). Aptamers, however, are smaller and less immunogenic than mAbs. AS-1411 (26 mer, 7.8 kDa) is a single stranded DNA that forms a G-quartet homodimer structure.

Binding of AS-1411 to nucleolin activates various biological cascades in cancer cells. One of the effects is destabilization of the anti-apoptotic bcl-2 mRNA. The degradation of bcl-2 mRNA subsequently triggers apoptosis in cancer cells. Although the testing of AS-1411 in clinical trials of myeloid acute leukemia and renal cell cancer is a positive sign of potential, there are concerns about the fate of the free drug in patients because of its fast clearance and pre-mature degradation before reaching the tumor (Stuart, R. K. et al., *J Clin Oncol* 2009, 27; Miller, D. M. et al., *Ann Oncol* 2006, 17, 147-148; Kim, B. Y. et al., *The New England journal of medicine* 2010, 363, 2434-43; Peer, D. et al., *Nat Nanotechnol* 2007, 2, 751-760).

It is therefore desirable to provide a method for transporting aptamers such as AP-1411 to a cancer cell for maximum anti-cancer effects. Such methods should not be specific to any one type cell, and indeed should be universal to many different cancer cell lines.

SUMMARY OF THE INVENTION

In light of the foregoing, it is an object of the present invention to provide a method of inducing changes to a nuclear phenotype of a cell comprising transporting a nanoconstruct comprising an aptamer, such as for example AS-1411 (Apt), and a gold nanostar (AuNS) to a nucleus of a cell, and releasing the aptamers from the surface of the gold nanostar into the nucleus of the cell to afford deformations or invaginations in the nuclear envelope (membrane), thereby inducing changes to the nuclear phenotype. The construct can be transported, or shuttled, to the nucleus via the nucleolin shuttling pathway. The aptamer can be released from the surface of the gold nanostar by, for example, exposing the nanoconstruct with near infrared light. Cells with more NE invaginations show increase in, for example, caspase activity (apoptosis of the cell), and preferably caspase 3 and 7 activity, as well as decreased cell viability. This correlation between drug-induced changes in nuclear phenotype and improved therapeutic efficacy provides for nuclear-targeted treatment, such as, for example, the treatment of cancer.

It is another object of the invention to provide a two-component nanoconstruct comprising an aptamer, such as Apt, and a gold nanostar. The construct is shown to increase the therapeutic and delivery efficiency of the aptamer in the treatment of conditions such as cancer.

It is still another object of the invention to provide a method for treating a hyperproliferative cell disorder, such as for example cancer, in an individual, the method comprising administering to the individual a nanoconstruct comprising an aptamer, such as for example Apt, and a gold nanostar, in an amount effective to reduce cell proliferation. Reduction of cell proliferation can be by way of, for example, the aptamer inducing apoptosis. The method can further comprise transporting the nanoconstruct to a nucleus of a cancer cell, providing nuclear envelope (NE) invaginations near a site of the nanoconstruct, and releasing the aptamers from the surface of the gold nanostar into the nucleus of the cancer cell to afford deformations in the nuclear envelope, thereby inducing changes to the nuclear phenotype. The method shows therapeutic selectivity of aptamer-AuNS nanoconstruct in cancer cells over normal cells. The method can also be applied to a broad range of metastic and primary tumor cells.

Accordingly, it will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

Other objects, features, benefits and advantages of the present invention will be apparent from this summary and the following descriptions of certain embodiments, and will be readily apparent to those skilled in the art. Such objects, features, benefits and advantages will be apparent from the above as taken into conjunction with the accompanying examples, data, and all reasonable inferences to be drawn therefrom. The disclosures in this application of all articles and references, including patents, are incorporated herein by reference.

DETAILED DESCRIPTION OF CERTAIN EMBODIMENTS OF THE INVENTION

Figure 1:
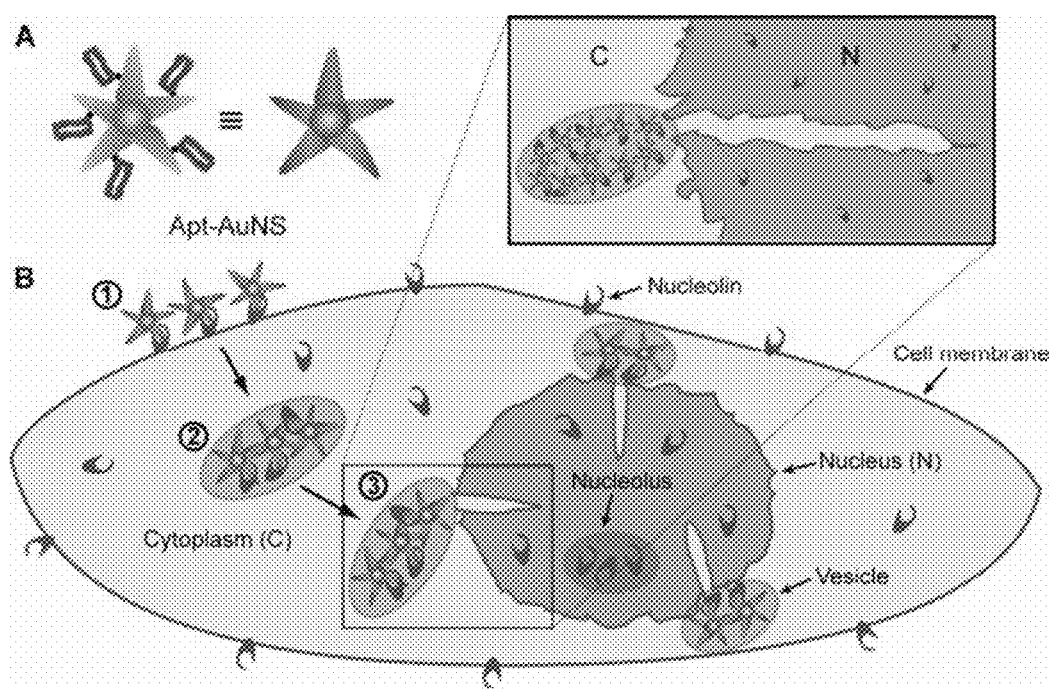
FIG. 1 depicts nucleolin-mediated, active trafficking of nanoconstructs to a cancer cell nucleus; (A) scheme of a two-component nanoconstruct (Apt-AuNS) consisting of nucleolin-specific aptamers AS-1411 and a gold nanostar (AuNS); and (B) scheme depicting delivery to the nucleus via three steps.

A first aspect of the present invention relates to a two-component nanoconstruct comprising an aptamer, such as for example, AS-1411 (Apt), and gold nanostars (AuNS). Such a nanoconstruct is observed interacting with cancer cell nuclei. The shuttling properties of nucleolin are exploited to traffic the nanoconstructs (Apt-AuNS) near the nucleus (FIG. 1) and then tested to determine how the nuclei-nanoconstruct interactions correlate with cell activity. Referring to FIG. 1, and illustrating a particular non-limiting embodiment of the invention, FIG. 1A is a scheme of a two-component nanoconstruct (Apt-AuNS) consisting of nucleolin-specific aptamers AS-1411 and a gold nanostar (AuNS). FIG. 1B is a scheme depicting delivery to the nucleus via three major steps: (1) binding of Apt-AuNS to surface-nucleolin receptors; (2) shuttling of Apt-AuNS by nucleolin to locations near the cell nucleus; and (3) interactions with the nuclear envelope (NE) of the nucleus. The inset in FIG. 1 shows that Apt-AuNS interactions with the nucleus result in deep, intruding folds of the NE into the nucleoplasm.

Figure 2:
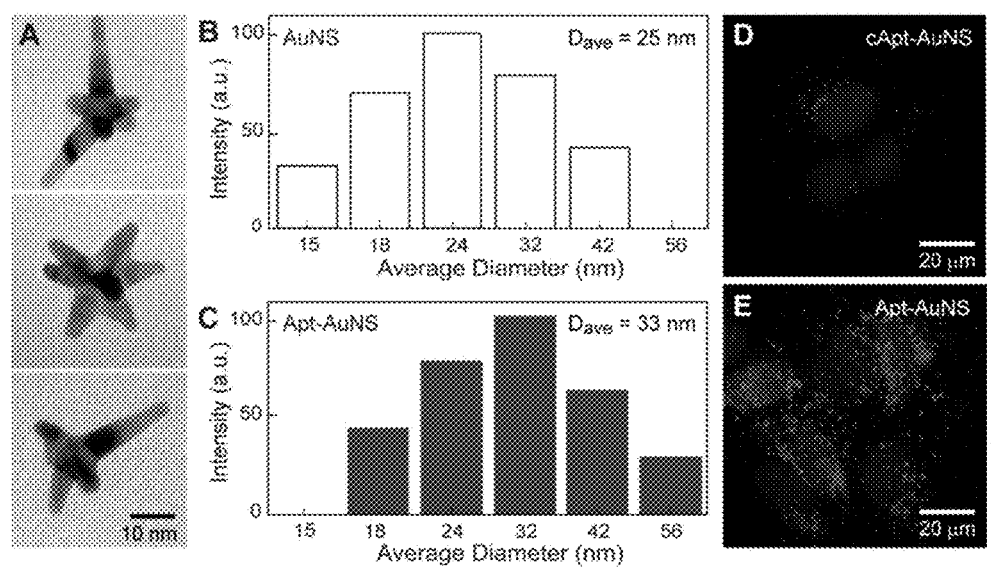
FIG. 2 shows surface functionalization and trafficking properties of nanoconstruct; (A) TEM images of biocompatible AuNSs; (B) hydrodynamic diameter of AuNSs before (as-synthesized) and (C) after conjugation with AS-1411 aptamer measured by dynamic light scattering; and (D) confocal fluorescence images of HeLa cells incubated for 7 h with Cy5-labeled control aptamer nanoconstructs (Cy5-cApt-AuNS) and (E) Cy5-labeled AS-1411 nanoconstructs (Cy5-Apt-AuNS).
Figure 7:
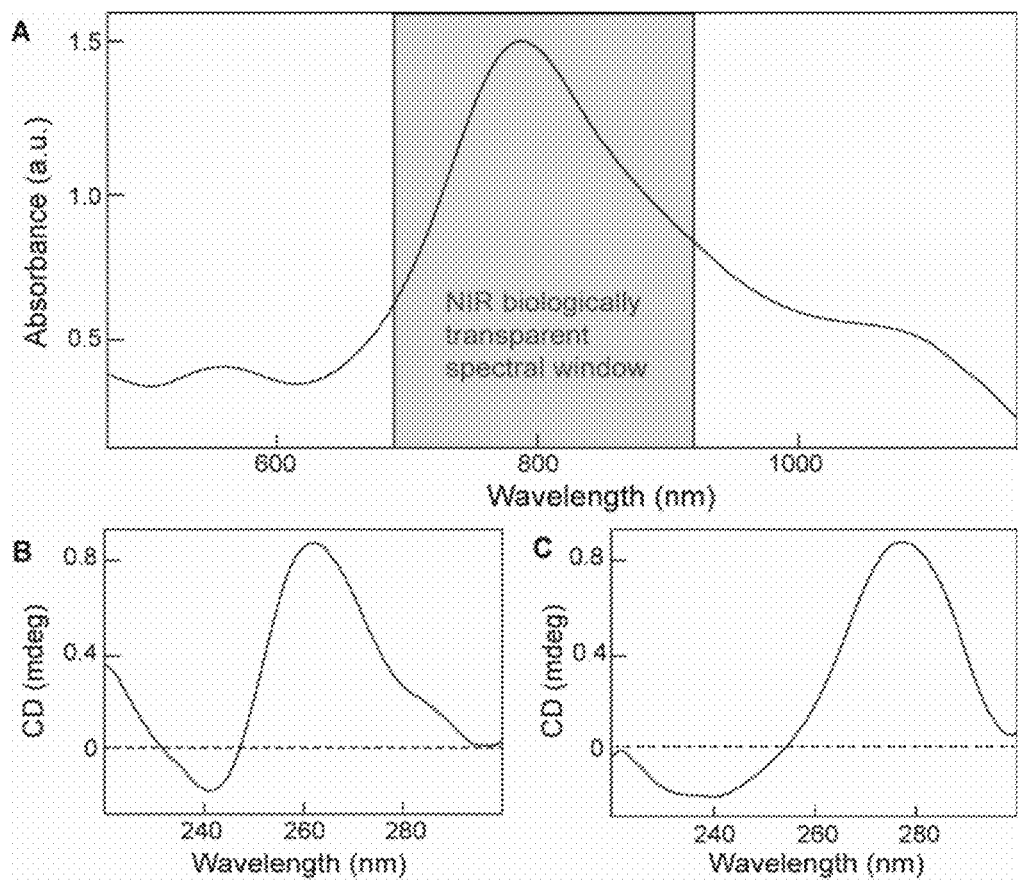
FIG. 7 shows the optical properties (confocal images) of AuNSs and structure of the aptamers; (A) the extinction spectrum of AuNS; (B) the circular dichroism (CD) spectrum of AS-1411; and (C) CD spectrum of the control nanoconstruct (cApt).

Biocompatible AuNS are synthesized by reducing Au (III) chlorate with 4-(2-hydroxyethyl)-1-piperazineethanesulfonic acid (HEPES) buffer (Xie, J. P. et al., 2007 *Chem Mater* 19, 2823, incorporated herein by reference). By controlling the ratio of the Au (III) salt to HEPES, multi-armed structures around 25 nm in diameter are produced as determined by high resolution transmission electron microscopy (HR-TEM) (FIG. 2A) and dynamic light scattering (FIG. 2B). These nanostars have a localized surface plasmon (LSP) resonance centered at 780 nm, which is within the biologically transparent near-infrared (NIR) spectral window (FIG. 7A). AS-1411 aptamers are conjugated to AuNSs via gold-thiol surface chemistry, as described in detail below. An increase in hydrodynamic diameter to 32 nm verifies the conjugation of the aptamers to the AuNSs (FIG. 2C). It is estimated that each AuNS supports ca. 950 AS-1411 dimers.

FIG. 7B shows the circular dichroism (CD) spectrum of AS-1411, wherein a positive peak at 265 nm and a negative peak at 241 nm are identified, which is characteristic of a G-quartet structure and in agreement with the CD spectrum of AS-1411 in previous work (Bates, P. J. et al., 2009 *Methods Mol Biol* 542, 379, incorporated herein by reference). Also, a control nanoconstruct (cApt-AuNS) is prepared, wherein the cApt has a cytosine-rich, non-quartet DNA structure (FIG. 7C; a dominant peak at 280 nm). This control sequence is selected because of its low affinity to nucleolin (Soundararajan, S. et al., 2008 *Cancer Research* 68, 2358; Bates, P. J. et al., 2009 *Experimental and Molecular Pathology* 86, 151, incorporated herein by reference).

In an embodiment of the invention, the trafficking properties of nucleolin for Apt-AuNS are tested by incubating Cy5-labeled nanoconstructs (Cy5-Apt-AuNS) with Henrietta Lacks (HeLa) cervical cancer cells for confocal fluorescence microscopy analysis. The Cy5-label is at the 3' end of the aptamer so the fluorescence is not quenched by the AuNSs. Confocal images shows that the fluorescence signals of the Cy5-Apt-AuNS overlap with the DAPI-stained (DAPI=4',6-diamidino-2-phenylindole) nucleus after a 5 hour incubation period (FIG. 8A). This signal co-localization increases when the incubation time increases to 7 hours (FIG. 2E) and up to 24 hours (FIG. 8A). In contrast, there is little overlap between the Cy5 and DAPI signals when the HeLa cells are treated with cApt-AuNS (FIG. 2D and FIG. 8B) for the same incubation times, i.e. the Cy5 signal is observed only in the cytoplasm and not in the cell nucleus. Together, these results suggest that the trafficking of the nanoconstructs by nucleolin occurs at locations spatially near the cell nucleus.

Figure 3:
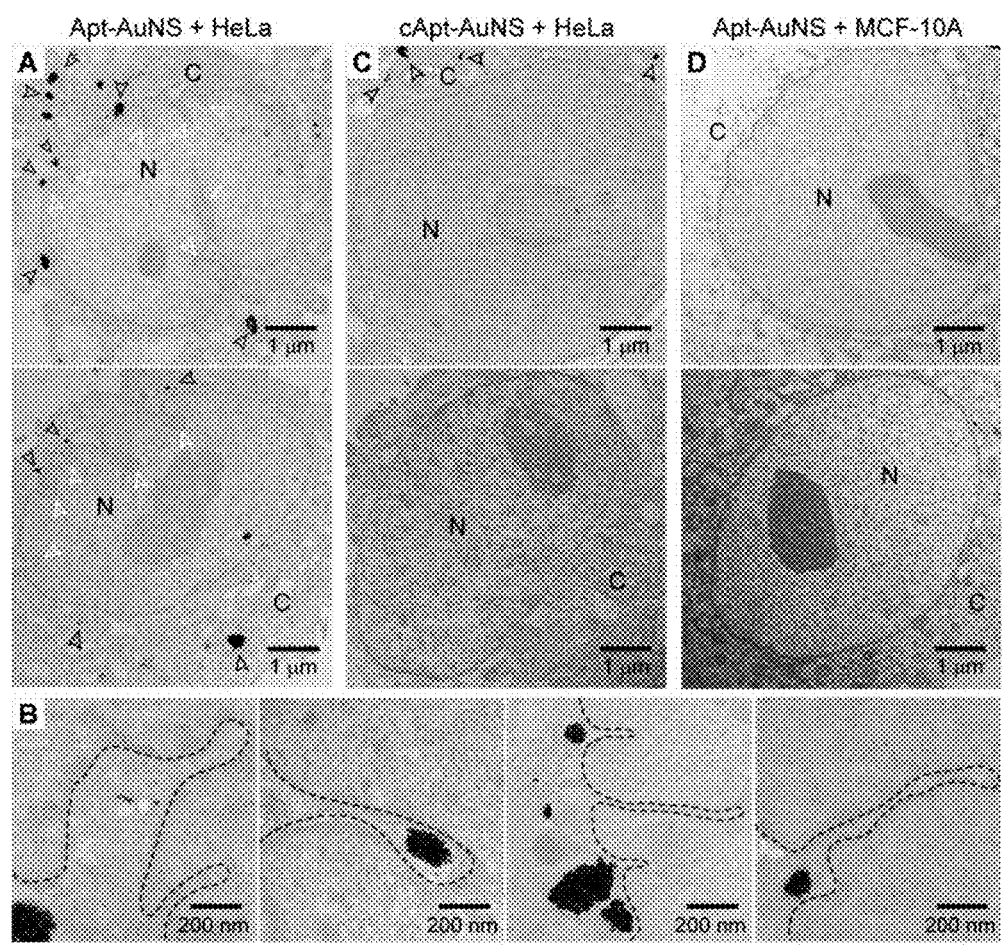
FIG. 3 shows nuclear envelope invaginations in cancer cell nuclei at locations near Apt-AuNSs; (A) TEM images of Apt-AuNS treated HeLa cells; (B) zoom-in images of portions of different nuclei; and (C) the nuclei of cApt-AuNS treated HeLa cells and (D) Apt-AuNS treated MCF-10A cells.

To determine the position of the nanoconstruct relative to the nucleus at the nanoscale level, HRTEM is used to image sections of HeLa cells incubated with Apt-AuNS for 7 hours. FIG. 3A shows that clusters of Apt-AuNS are localized in the cytoplasm (C) close to the nucleus (N). It is noted that in FIG. 3A, white arrows highlight the locations of the NE folds, while black arrows point to the Apt-AuNS clusters. In contrast, only a few clusters of cApt-AuNS are observed near the nucleus even after extensive searching (FIG. 3C). These results are consistent with the co-localization of the Cy5 and DAPI fluorescence signals in FIG. 2D. To verify that the transport of the Apt-AuNS in cancer cells is mediated by nucleolin, the same experiments are carried out except using MCF-10A, a normal mammary epithelial cell line lacking surface nucleolin. After 7 hours of incubation, only a minimal number of Apt-AuNSs anywhere inside the MCF-10A cells is found (FIG. 3D).

Figure 8:
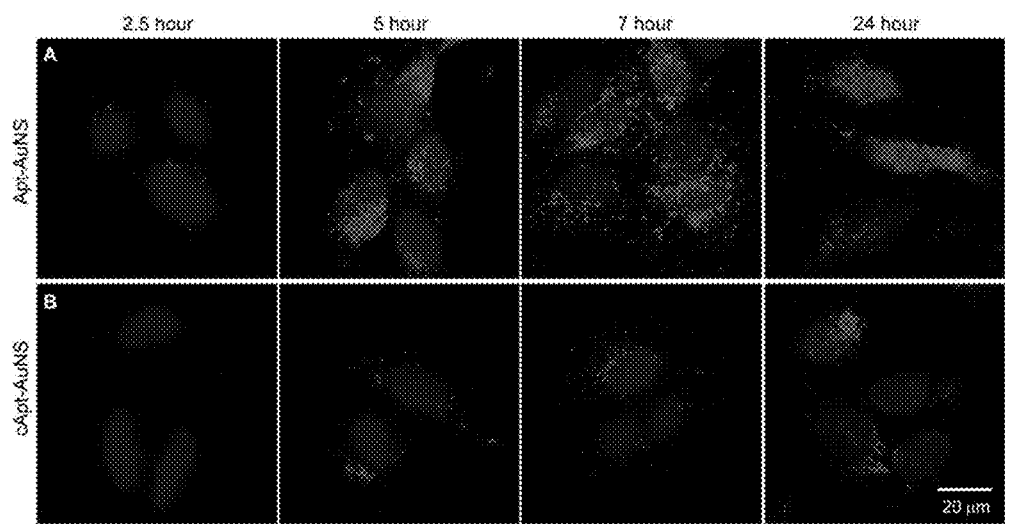
FIG. 8 depicts the intracellular trafficking of nanoconstructs to nucleus via imaging with confocal fluorescence microscope; (A) accumulation of Cy5-Apt-AuNS in the nucleus, indicated by the red fluorescence, starts to appear after 5 hours and increases significantly after 7 hours and 24 hours, respectively; and (B) HeLa cells treated with control nanoconstructs (Cy5-cApt-AuNS).
Figure 9:
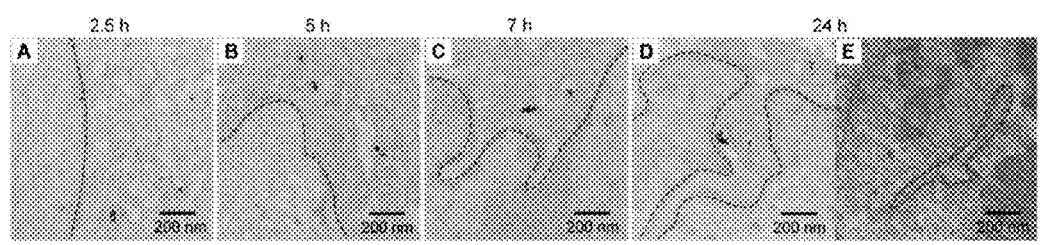
FIG. 9 (A) TEM image of a HeLa nucleus treated with Apt-AuNS after 2.5 hours of incubation; (B) after 5 hours of incubation; (C) after 7 hours of incubation; (D) after 24 hours of incubation; and (E) after 24 hours of incubation, cross-sections of the deep folds are observed inside the nucleoplasm.

Under higher magnification, TEM images reveal that the Apt-AuNS are in some type of vesicle throughout the intracellular trafficking process (FIG. 3B). Significantly, major changes in the nuclear phenotype are observed; the NE is extremely deformed in over 60% of the HeLa cells containing the nanoconstructs. To date, there have only been a few reports on folding in the NE, but none because of drug interactions (see Fricker, M. et al., 1997 *J Cell Biol* 136, 531, incorporated herein by reference). More importantly, the locations of these intruding folds into the nucleoplasm correlate directly with the location of the Apt-AuNS near the nucleus. Greater than 100 cell sections are analyzed to confirm the spatial correlation between the position of the vesicles containing Apt-AuNS and the sites of folding in the NE. Nearly all vesicles with nanoconstructs are located inside and close to the opening of the nuclear membrane folds (FIG. 3B), which strongly implies that the presence of the nanoconstruct results in localized changes in the cancer cell nucleus. Also, increasing incubation times of the nanoconstruct results in even deeper invaginations or multi-branched folds of the NE at 7 hours. Cross-sections of these deep folds within the nucleoplasm are observed over 24 hours (FIG. 9). Accordingly, no deformations of the nuclear envelopes (NE) are found after 2.5 hours of incubation with Apt-AuNS (FIG. 9A). FIGS. 9B-C show deeper invaginations and multi-branched folds of the NE observed at 5-hour and 7-hour incubations, respectively. After 24 hours of incubation, very deep NE folds intruded into the nucleoplasm (FIG. 9D) and cross-sections of the deep folds (FIG. 9E) are observed inside the nucleoplasm. These results agree with the incubation time-dependent confocal fluorescence data (FIG. 8).

Figure 10:
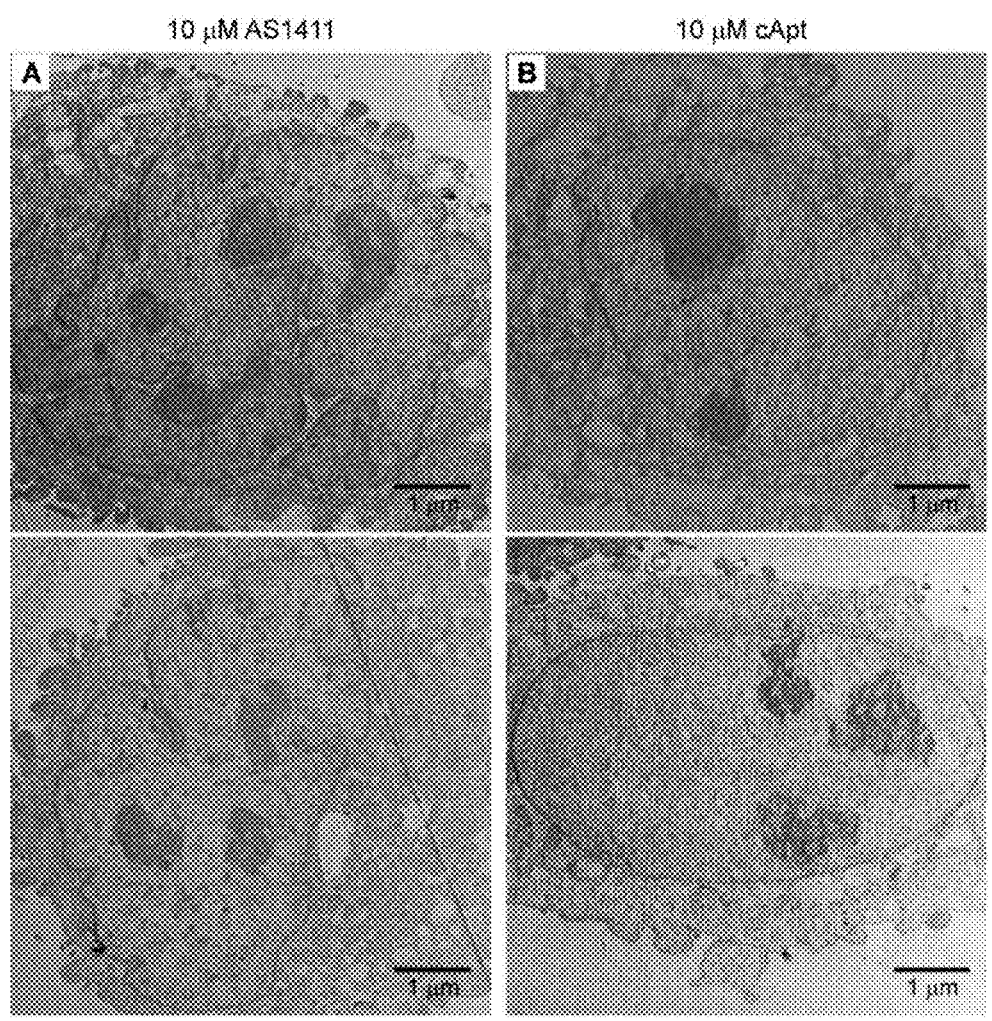
FIG. 10 provides TEM images comparing nuclei of HeLa cells after treatment with free AS-1411 and the free control aptamers; (A) HeLa cells treated with a therapeutic concentration (10 µM) of free AS-1411 and (B) 10 µM of the free control aptamer.

Since NE folding is only observed in cancer cells treated with Apt-AuNS but not cApt-AuNS, it is hypothesized that the AS-1411 aptamers are primarily responsible for NE folding. Experiments are conducted with free AS-1411, and NE folding in ca. 70% of the HeLa cell population after treatment at therapeutic concentrations (10 µM) is observed (FIG. 10A). In contrast, and in agreement with the cApt-AuNS results, no deformations are found in the nucleus after treatment with the free control aptamer (FIG. 10B). These results indicate that the Apt-AuNS vesicles interact with the cell nucleus via the aptamers even though the uptake mechanism is most likely by endocytosis.

Figure 11:
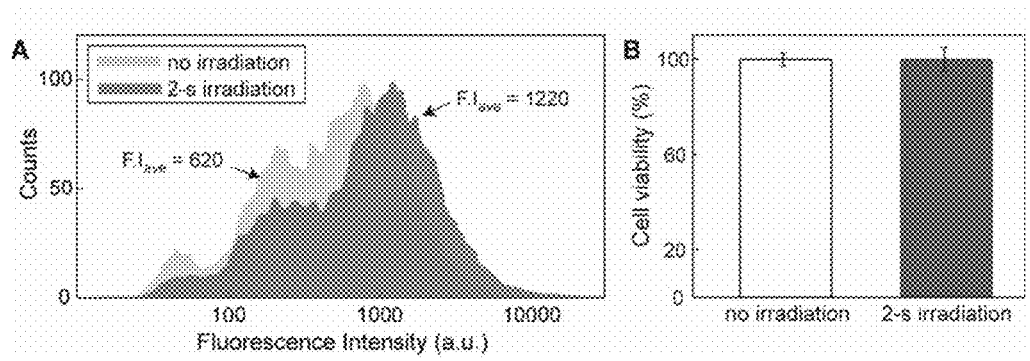
FIG. 11 (A) flow cytometry of HeLa cells treated with Cy5 labeled Apt-AuNS (Apt-Cy5-AuNS); (B) graph of cell viability assays show minimal influence of the laser pulses on the HeLa cells in the absence of the Apt-AuNS.

In yet another embodiment, to test whether the concentrated release of aptamer from the nanoconstructs increases NE folding further, AS-1411 are detached from the AuNS surface using femtosecond (fs)-pulses at the LSP wavelength of the AuNSs (ultra-fast pulses at NIR wavelengths have been used to detach thiolated DNA from gold nanoparticles while maintaining the viability of the molecules; see Wijaya, A. et al., 2009 *ACS Nano* 3, 80; Jain, P. K. et al., 2006 *J Am Chem Soc* 128, 2426, incorporated herein by reference). Optimized irradiation conditions (e.g. shortest excitation time, lowest pulse energy) are identified using Cy5-labeled Apt-AuNS incubated with HeLa cells for 7 hours. For these experiments, the Cy5 is situated at the thiol end of the aptamer (closest to the AuNS surface, Apt-Cy5-AuNS) so that only if the AS-1411 aptamer is released from the AuNSs is fluorescence observed. In buffer, 40-fs pulses with a power density of 4.8 W/cm$^2$, irradiation time of 2 seconds, and wavelength of 800 nm produces the largest fluorescence signal, and hence, the highest amount of AS-1411 release. Flow cytometry of HeLa cells and Apt-Cy5-AuNS irradiated with NIR fs-pulses show a two-fold increase in Cy5 fluorescence intensity compared to non-irradiated samples (FIG. 11A), which shows that the aptamers are being released from the Apt-AuNSs. In FIG. 11A, irradiation conditions are as follows: pulse duration=40 fs; power density=4.8 W/cm$^2$; irradiation time=2 seconds; frequency=1 kHz; wavelength=800 nm). FIG. 11B is a graph of the cell viability assays, which show minimal influence of the laser pulses on the HeLa cells in the absence of the Apt-AuNS.

Figure 4:
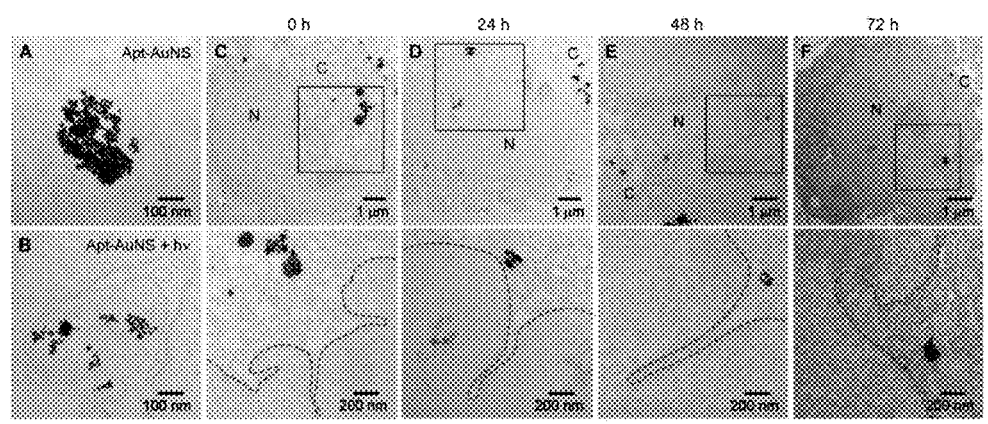
FIG. 4 (A) is a TEM image depicting the vesicle membrane surrounding the Apt-AuNS clusters conforms to the particles and is intact; (B) TEM image shows vesicle membranes are partially deteriorated after irradiation; and (C) TEM image of nuclei of HeLa cells treated with Apt-AuNS and followed by irradiation immediately, (D) after 24 hours, (E) after 48 hours, and (F) after 72 hours after the aptamers are released.

HeLa cells incubated with Apt-AuNS exhibit several distinct effects after fs-irradiation. First, the vesicle membrane surrounding the Apt-AuNS partially deteriorates (FIG. 4B), which allows the released aptamers to escape from the vesicles. Possible heating effects cannot be eliminated, but this temperature increase is minimal, as reported in Wijaya, A. et al. and Jain, P. K. et al. Second, greater than 95% of the cells containing Apt-AuNS show deformations in nuclear phenotype and NE invaginations immediately after irradiation (FIG. 4C). This 40% increase in the number of cells that show NE folding (compared to 60% without released aptamer) suggests that the released aptamers interact with more cancer cell nuclei. The effects of the released drug over longer times are studied by examining the cancer cell nucleus at 24, 48, and 72 hours after aptamer release. At 24-hour and 48-hour time points, the NE invaginations are deeper, and the overall number of NE folds increases by about 2 times (FIGS. 4D-E). After 72 hours, 98% of the cell population is composed of small daughter cells that show extreme NE roughening (FIG. 4F). These observations suggest that the released AS-1411 continues to have an effect even after 72 hours.

Figure 5:
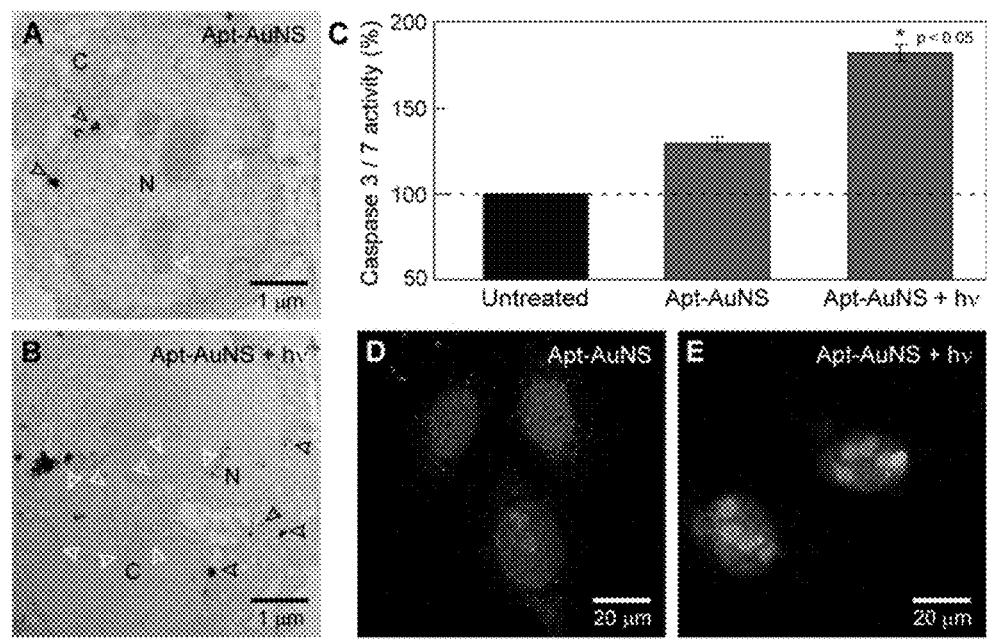
FIG. 5 (A) TEM image of a HeLa nucleus treated with Apt-AuNS after incubation for 7 hours; (B) TEM image showing a dramatic increase in the number and depth of the NE invaginations after fs-pulsed irradiation for 2 seconds; (C) graph of caspase 3 and 7 activity of Apt-AuNS treated HeLa cells immediately after irradiation ($p<0.05$); and (D) confocal fluorescence image of double stranded DNA breaks (DSBs) indicated by the green FITC fluorescence in HeLa cells incubated with Apt-AuNS only and (E) Apt-AuNS and light-triggered release of aptamer.

Direct comparison of the HeLa cell nuclei before and after fs-irradiation indicates that an increase in number of NE folds (>two-fold) is observed immediately after the AS-1411 is released from the AuNSs (FIG. 5A-B, wherein white arrows highlight the locations of the NE folds and black arrows point to the Apt-AuNS cluster). To test whether these physical changes correlate to cell function, caspase 3 and 7 activities are measured, since an increase in caspase activity suggests that cells are undergoing apoptosis (Schwartz, G. K. et al., 2005 *J Clin Oncol* 23, 9408, incorporated herein by reference). FIG. 5C shows that the caspase activity of HeLa cells treated with Apt-AuNS+hv increases immediately by 1.5 times compared to cells incubated with only Apt-AuNS. In addition, since apoptosis is related to the functional disruption of the nucleus (Kang, B. et al., 2010 *J Am Chem Soc* 132, 1517, incorporated herein by reference), the amount of double-stranded DNA breaks (DSBs) is evaluated by confocal fluorescence microscopy (FIGS. 12A-D). FIGS. 5D-E show that DAPI-stained nuclei overlap with the green FITC fluorescence of the DSB foci. Clearly, the DSB foci of Apt-AuNS treated cells exhibit significantly higher FITC signals after aptamer release from the AuNS carriers (FIG. 5E). Therefore, the increases in caspase activity, as well as the increase in DNA damage, are highly correlated to the increased levels of NE deformation.

Figure 6:
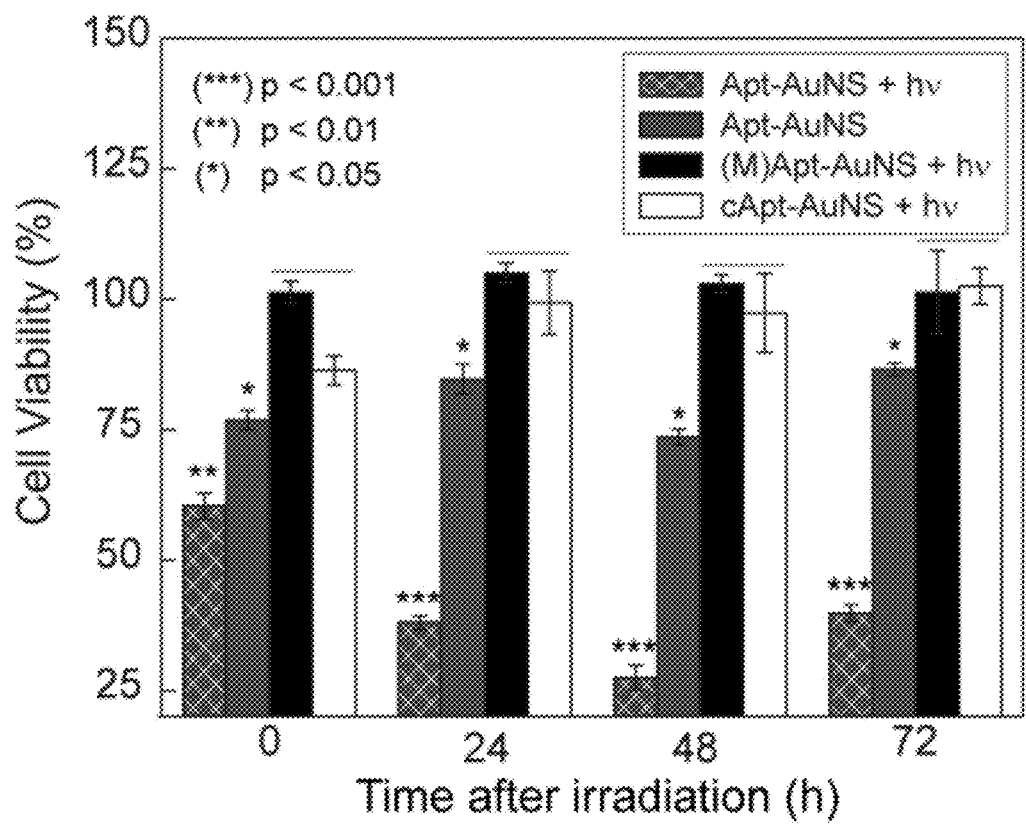
FIG. 6 shows viability analysis of Apt-AuNS treated HeLa cells.

In still another embodiment, the hypothesis of whether the physical deformation of the NE correlates with changes in cellular activities such as metabolism is tested. Cell viability is measured, since a decrease in viability indicates shutdown of metabolic activity, as discussed in Schwartz, G. K et al. HeLa cells treated with both Apt-AuNS only and Apt-AuNS+hv show decreased cell viability over 72 hours. Consistent with the increased amounts of NE folding, 40% of the HeLa cell population treated with Apt-AuNS+hv die immediately, while only 25% of the population die with Apt-AuNS (FIG. 6, wherein lines over bars indicate groups that are not significantly different). This result confirms that locally increasing the availability and concentration of the AS-1411 near the cell nucleus can have deleterious effects on the metabolic activity of the cells (p<0.01) and result in cell death. Furthermore, viability analysis shows that greater than 70% of the cell population dies between 48 and 72 hours after release of the aptamer, a percentage that is much higher than that of Apt-AuNS only treated cells (ca. 25%). In addition, the viabilities of cApt-AuNS treated HeLa cells and Apt-AuNS treated MCF-10A cells after ultrafast light irradiation are nearly 100%. This result is expected since the nuclei of these cells remains intact (FIG. 3C-D) and indicates that the 2-s light irradiation does not cause cell damage. These experiments strongly suggest that the physical deformation of the nucleus is related to the prolonged shutdown of cellular metabolism.

Figure 15:
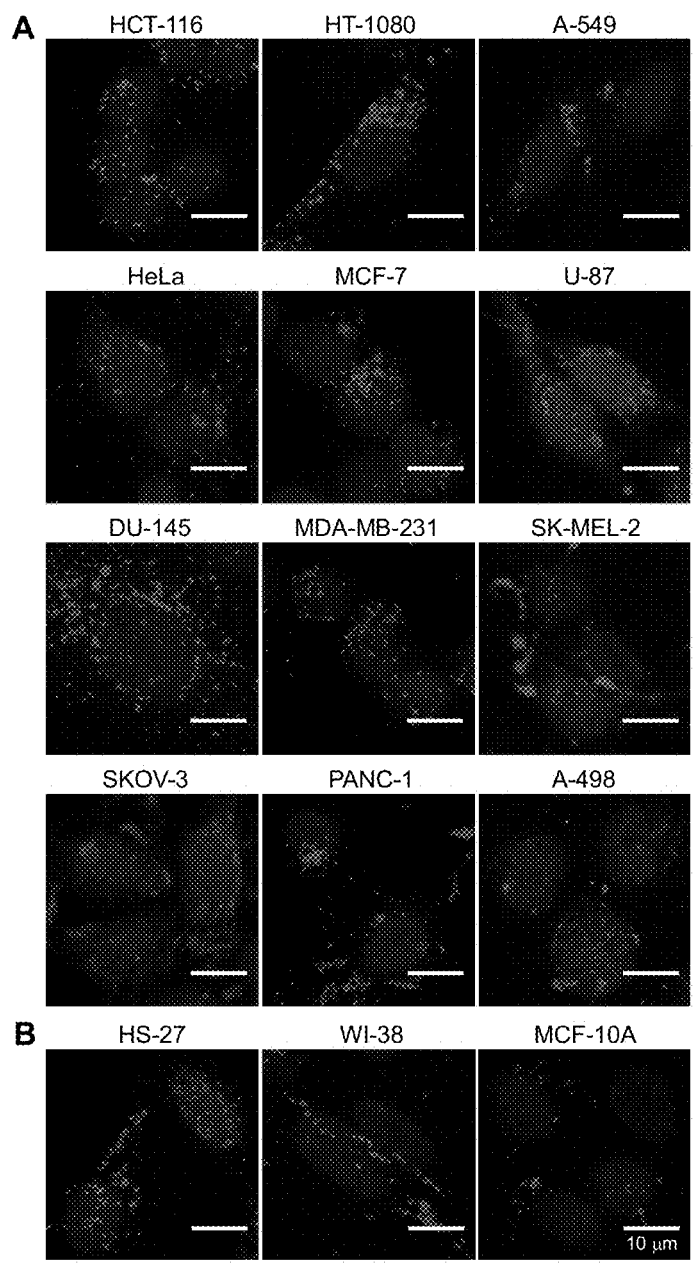
FIG. 15 provides confocal fluorescent images of the uptake of Apt-AuNS in various (A) cancer cells and (B) normal cells.
Figure 16:
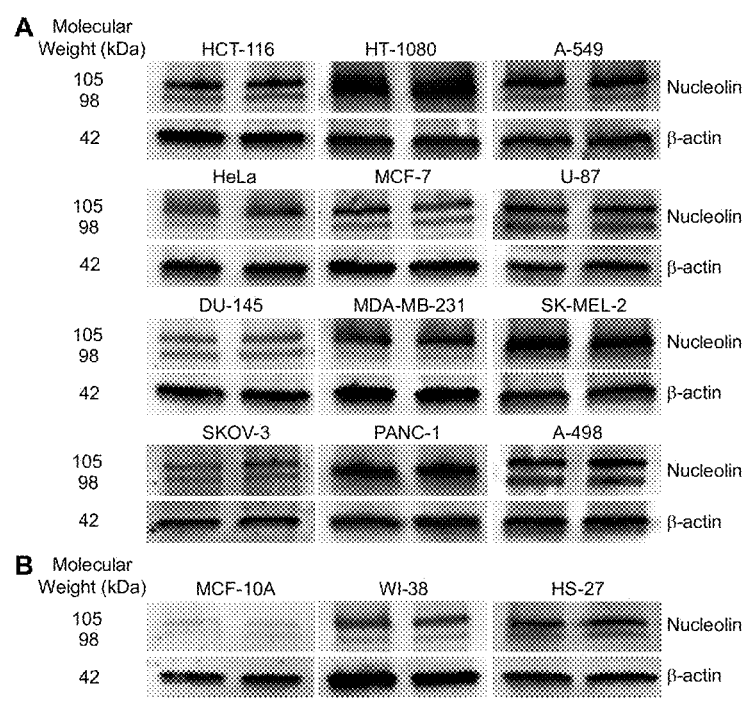
FIG. 16 provides imminoblots of the cytosolic extracts of various (A) cancer cells and (B) normal cells.

In another embodiment, the shuttling delivery and the anti-cancer effects induced by Apt-AuNS-nucleolin interaction are not specific to one type of cancer cell, but can be universal to many cancer cell lines. Specifically, eleven cancer cells that have previously shown susceptibility to free AS-1411 are used to compare the efficacy of Apt-AuNS to free drugs. SKOV-3, an ovarian carcinoma cell that has not yet been tested with AS-1411, is also included in the cancer cell panel. In addition, HS-27 and WI-38, normal skin and lung fibroblasts, and MCF-10A, an epithelial mammary cell, are used to test the effects of Apt-AuNS on normal tissue. To determine the intracellular localization of Apt-AuNS, confocal images of cancer and normal cells after a 7-hour incubation with 0.3 nM of the nanoconstruct are collected. FIG. 15A shows accumulation of Cy5-labeled Apt-AuNS (red fluorescence) in the cytoplasm and near the DAPI-stained nucleus (blue fluorescence) in all the cancer cells. This accumulation of Apt-AuNS, however, is also found in normal cells, especially fibroblast type (FIG. 1B). This phenomenon accords with observations reported by Reyes-Reyes et at (Reyes-Reyes, E. M. et al., *Cancer Res* 2010, 70, 8617-8629, incorporated herein by reference). The exact gold (Au) content in the cancer cells using inductively coupled plasma-mass spectrometry (ICP-MS) is determined. Gold content is found in all 12 cancer cell lines with the highest level in pancreatic cancer cells, PANC-1 (~24 ppt/cell) (FIG. 16A). Significant amounts of Au are also found in fibroblast cells HS-27 and WI-38 (~10 ppt/cell). However, the Au level is much lower in mammary epithelium cells MCF-10A (~2 ppt/cell). These results agree with the abundant Cy5 signals that are observed in fibroblast cells by confocal microscopy.

Figure 17:
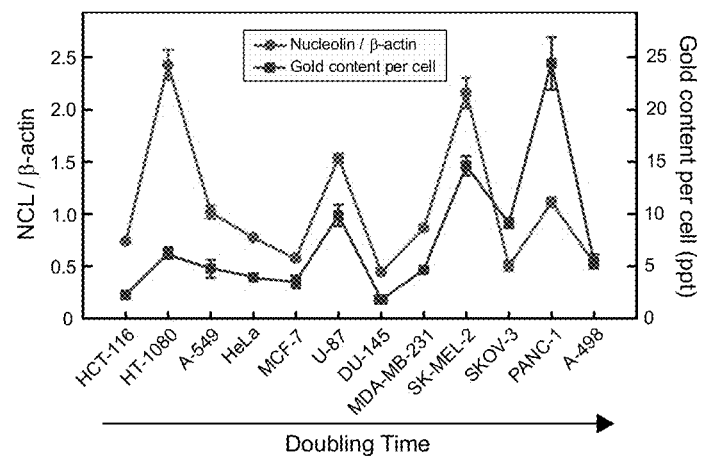
FIG. 17 is a graph that shows a correlation between the level of nucleolin and the uptake of Apt-AuNS in cancer cells.

Because Apt binds to nucleolin to be internalized by cancer cells, the relative amounts of nucleolin in the cytosolic compartment of cancer and normal cells is determined to establish whether differences in nucleolin levels can be related to the uptake of Apt-AuNS (Soundararajan, S. et al., *Mol Pharmacol* 2009, 76, 984-991; Hovanessian, A. G. et al., *Plos One* 2010, 5, incorporated herein by reference). The cytosolic extracts of cancer and normal cells are analyzed by immunoblotting to permit measurement of nonnuclear nucleolin. The relative amounts of nucleolin in these extracts are calculated after normalization to housekeeping protein, β-actin. The analysis reveals that full-length nucleolin (106 kDa) and its proteolysis product (98 kDa) in the extracts of cancer cells is up to 25 times greater than that of normal cell, MCF-10A (FIG. 16A). Unexpectedly, the levels of nucleolin found in the non-nuclear extracts of Hs-27 and WI-38 fibroblast cells are comparable to that in some cancer cells and 5 to 7 times higher than that of MCF-10A (FIG. 16B). Again, these results agree with relative high uptake of Au content observed in these fibroblast cells. FIG. 17 shows a correlation between the level of nucleolin and the uptake of Apt-AuNS in cancer cells. Increased nucleolin levels result in higher uptake of Apt-AuNS. This correlation, however, is not directly proportional due to different doubling times among the cells in the panel. Cancer cells with long doubling time (>40 hours) and high expression of nucleolin (e.g. PANC-1 and SK-MEL-2) appear to uptake larger amount of Apt-AuNS than those with short doubling time (<24 hours) and low expression of nucleolin (e.g. HCT-116 and DU-145) (FIG. 17).

Figure 18:
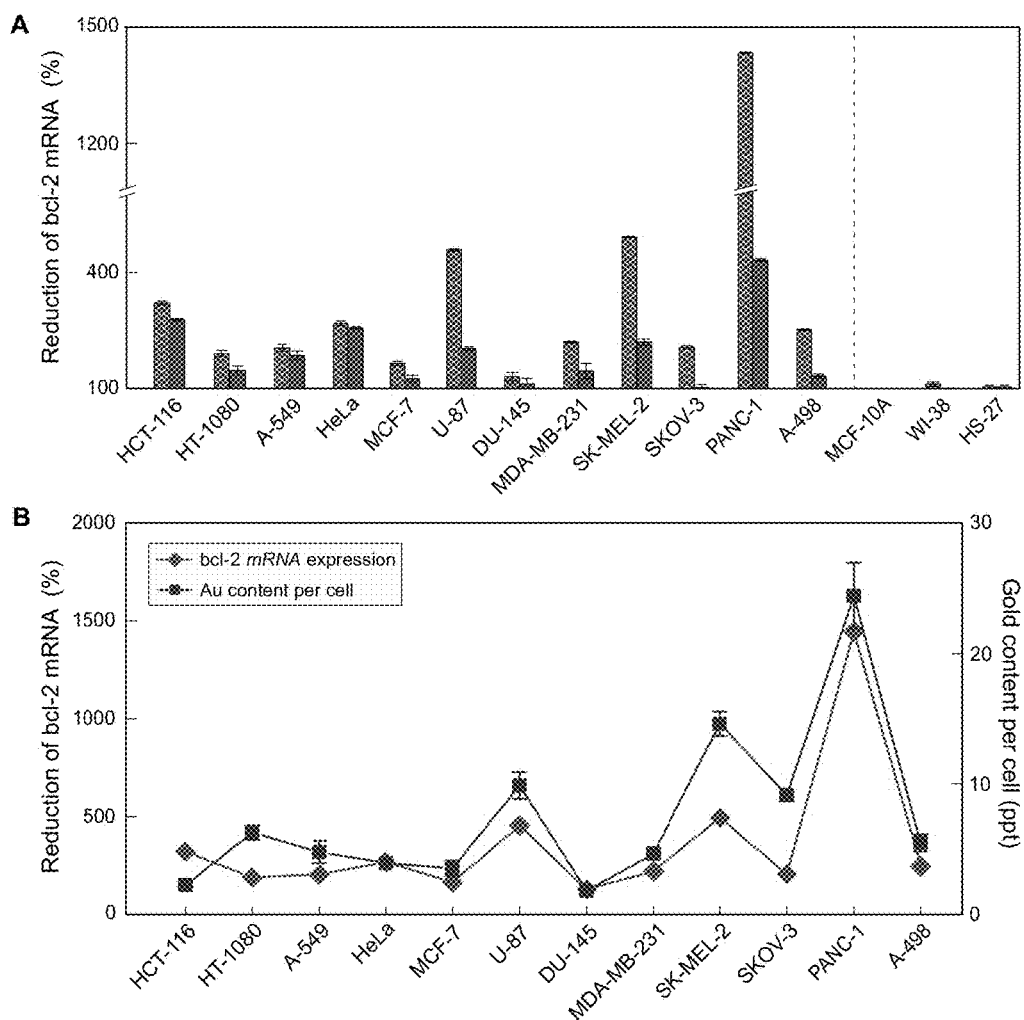
FIG. 18 (A) is a graph showing the expression level of anti-apoptotic bcl-2 mRNA in cancer cells and normal cells after treatment with Apt-AuNS+hv; (B) is a graph showing correlation between uptake of Apt-AuNS and reduction of bcl-2 mRNA expression.

One function of nucleolin is to bind to an AU-rich element instability component in the 3'-untranslated region (UTR) of mitochondrial bcl-2 mRNA and protect the mRNA from degradation (Otake, Y. et al., *Blood* 2007, 109, 3069-3075; Sengupta, T. K. et al., *J Biol Chem* 2004, 279, 10855-10863, incorporated herein by reference). Free AS-1411 interferes with the stabilization of bcl-2 mRNA by binding to nucleolin. This phenomenon results in degradation and downregulation of the mRNA. Experiments are conducted to determine whether Apt-AuNS exhibits similar inhibition of nucleolin-bcl-2 mRNA interaction that causes reduction of mRNA expression. Using quantitative real-time polymerase chain reaction (RT-PCR), 1.5-4-times reduction of bcl-2 mRNA expression is observed across the cancer cells panel after treatment with Apt-AuNS compared to cancer cells that did not go under treatments (FIG. 18A). The result suggests that treatment with Apt-AuNS down-regulates bcl-2 mRNA in cancer cells. Furthermore, the expression of bcl-2 gene reduces significantly (2-15 times) in all 12 cancer cell lines after treatment with Apt-AuNS+hv. PANC-1 cells show the largest decrease of 15-fold in the expression of the bcl-2 gene (FIG. 18A). This elevated effect after the release of Apt from AuNS appears to correlate strongly with increased levels of NE folding in the cancer cells. The levels of bcl-2 mRNA in normal cells remain unchanged after any treatments (FIG. 18A). This result accords with minimal physical damages in the nuclei of the normal cells.

Because interaction with nucleolin is an important activity for stabilization and expression of the bcl-2 gene in cancer cells, inhibition of this interaction by Apt-AuNS reduces the levels of bcl-2 mRNA. Thus, the issue of whether uptake levels of Apt-AuNS affect the regulation of the bcl-2 gene is determined. Results indicate that cancer cells with higher uptake of Apt-AuNS show larger decline in bcl-2 mRNA expression with the exception of HT-1080 (FIG. 18B). This exception, however, is explained by initial high levels of nucleolin in the cytosolic extract of HT1080 (FIG. 17), which increases the stability of bcl-2 gene. The data is in agreement with previous findings in Soundararajan, S. et al., which recites that with free Apt, an increase concentration of Apt reduces the enrichment of bcl-2 mRNA in cancer cells. Altogether, Apt-AuNS shows similar activity as free Apt by interfering with bcl-2 mRNA-nucleolin interaction and eventually decreasing expression of the mRNA in cancer cells.

Figure 19:
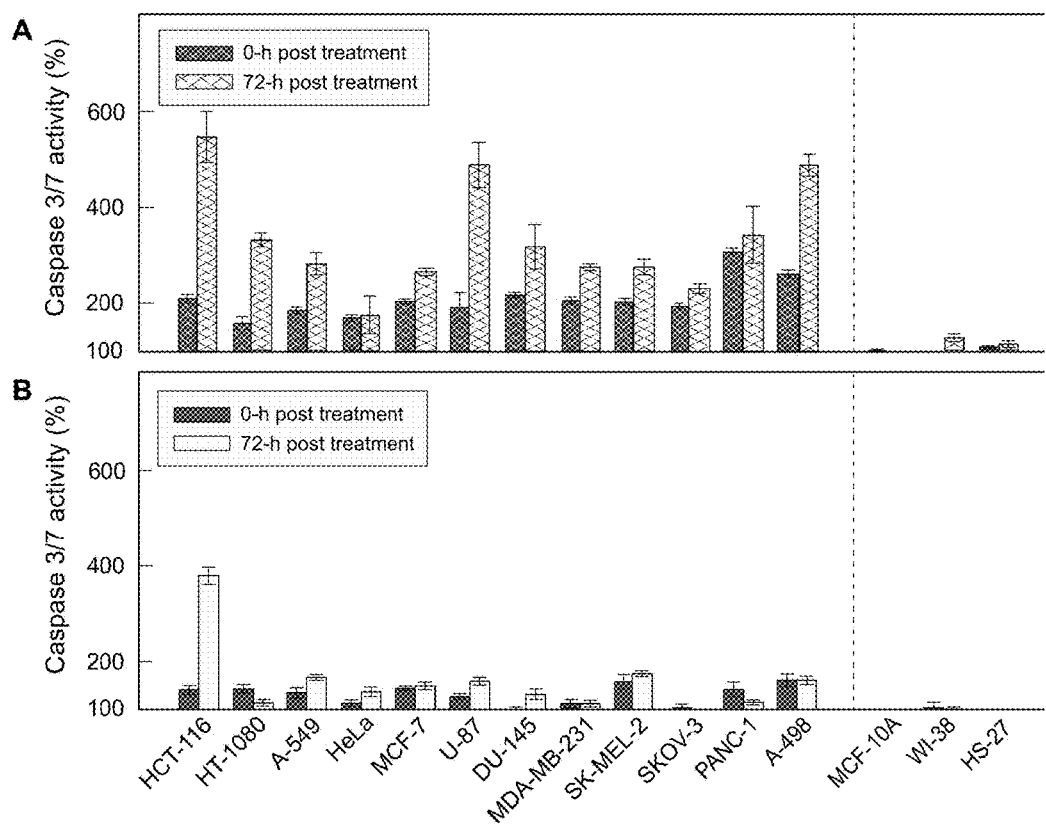
FIG. 19 is a graph showing the caspase 3/7 activities in samples treated with (A) Apt-AuNS+hv and (B) Apt-AuNS.
Figure 20:
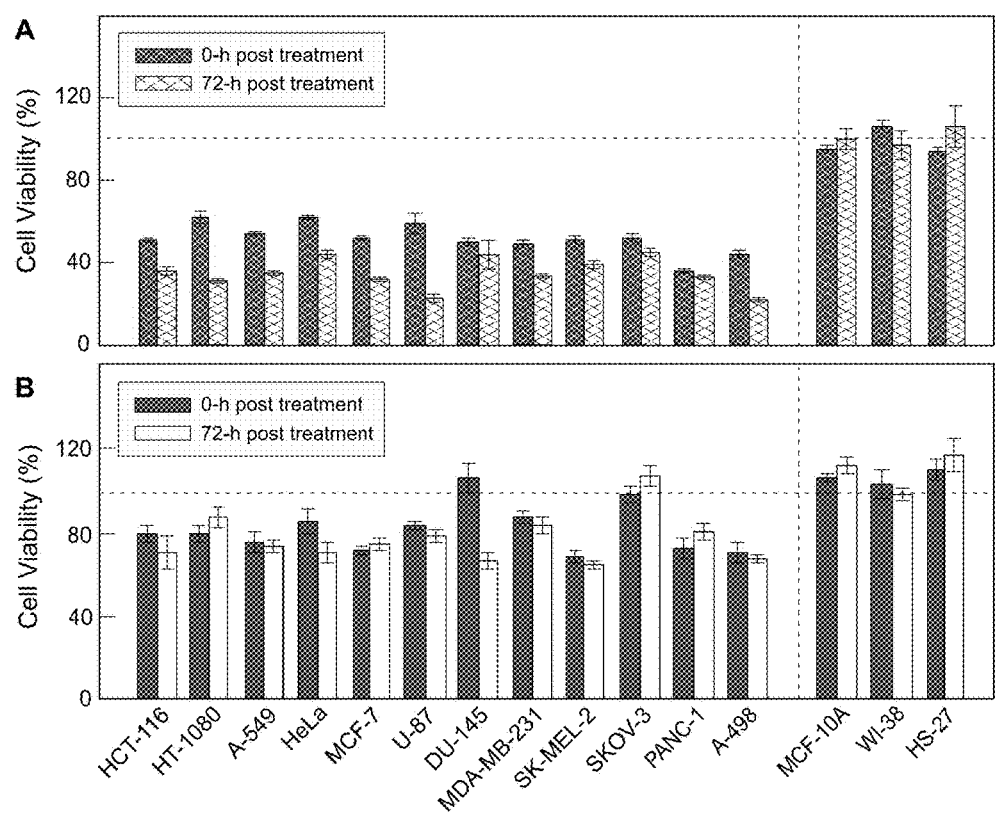
FIG. 20 (A) is a graph of cell viability analysis after light-triggered release of the aptamer; (B) is a graph of cell viability analysis of Apt-AuNS without releasing the aptamer.

Reduced expression of bcl-2 mRNA can trigger apoptosis in cancer cells, which can be detected by elevation of the caspase 3 and 7 activities. Thus, the caspase 3/7 activities are measured in 12 cancer cell lines and increases of up to 3 times are observed immediately after a single treatment with Apt-AuNS+hv. Although the cancer cells are only treated once with Apt-AuNS+hv, the caspase activities elevate up to 6 times in all cells when measured at 72 hours after the treatment (FIG. 19A). These results suggest that one-time release of the Apt from AuNS induces prolonged biological effects on cancer cells. Cell viability of these cancer cell lines shows a minimum of 40% decrease right after light-triggered release. The amount of cell death increases up to 80% after 72 hours (FIG. 20A). Also observed is a parallel relationship between changes in caspase activities/cell death and NE folding. For instance, caspase 3/7 activities and cell death are higher (2-3 times) in all cancer cells with increased level of NE folding after treatment with Apt-AuNS+hv compared to those treated with Apt-AuNS (FIGS. 19B & 20B). In contrast, both the caspase 3/7 activities and cell viability do not change in normal cells after undergoing the same treatments (FIGS. 19 & 20). This observation suggests that the normal cells do not enter the apoptotic programmed cell death, which agrees with minimal reduction in bcl-2 mRNA expression.

Figure 21:
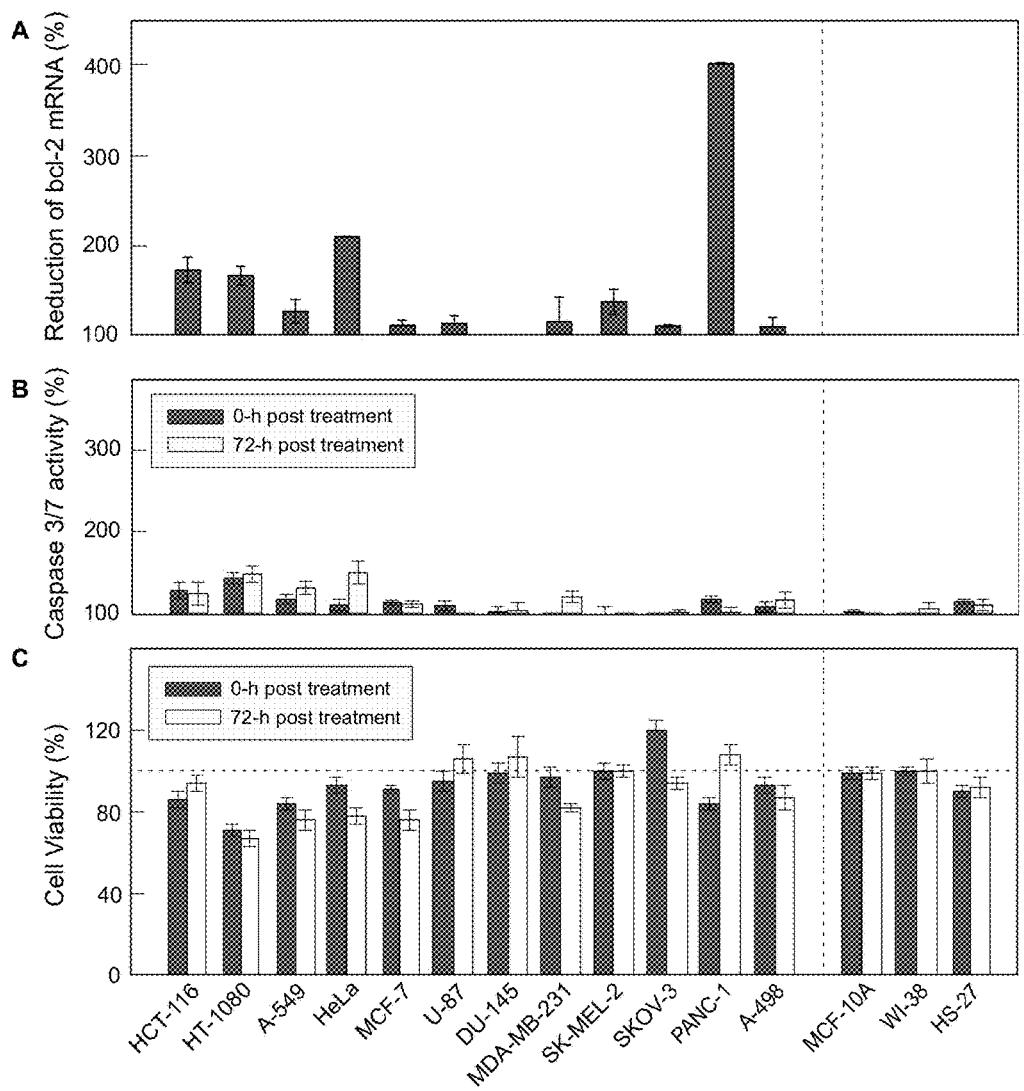
FIG. 21 shows the effects of free AS-1411 on cancer cells and normal cells; (A) is a graph showing bcl-2 mRNA expression; (B) is a graph showing caspase 3/7 activities; and (C) is a graph of cell viability.

In vitro growth inhibition by free AS-1411 is previously observed after 4 days of continuous exposure at low micromolar (2 μM) concentrations (Dapic, V. et al., *Biochemistry-Us* 2002, 41, 3676-3685, incorporated herein by reference). A seven day exposure of leukemia and lymphoma cells to 10 μM AS-1411 results in over 60% cell death (Ireson, C. R. et al., *Mol Cancer Ther* 2006, 5, 2957-2962, incorporated herein by reference). Although free Apt shows therapeutic effects on cancer cells, micromolar range concentrations of Apt are used. To demonstrate the advantage of light-triggered release treatment of the instant invention, a side-by-side comparison between cancer cells treated with Apt-AuNS+hv and those treated with 450 nM free AS-1411, an equivalent concentration of AS1411 on the surface of AuNS assuming that all Apt is released, is conducted. The expression of bcl-2 mRNA in cancer cells treated with 450 nM free AS-1411 only decreases by minimal amounts (1.2 to 2 folds) compared to those treated with Apt-AuNS+hv (FIG. 21A). In addition, while over 80% cell death is observed in all cancer cells 72 hours after treatment with Apt-AuNS+hv, only five out of 12 cancer cells treated with free AS-1411 show approximately 20% cell death with small increase (<1.2 fold) in caspase 3/7 activities (FIGS. 21B & 21C). This is attributed to the superior efficacy of the light-triggered released Apt-AuNS to three main factors: 1) Apt attached to AuNS is less susceptible to degradation by serum or DNase than the free Apt, hence more Apt reaches the cancer cells; (2) because Apt are tightly packed on the AuNS, more than one Apt are delivered to cancer cells at once. Thus, aptamers integrated with AuNS are internalized by cancer cells more effectively than the free Apt; and (3) because the light-triggered release creates a high-localized concentration of Apt at locations close to the nuclei of cancer cells, only nanomolar concentration of Apt-AuNS (0.3 nM) are required to generate potent anti-cancer effects. This phenomenon cannot be achieved by free Apt without using high dosages.

EXAMPLES

The following non-limiting examples and data illustrate various aspects and features relating to the methods and compositions of the present invention. In comparison with the prior art, the present compositions and/or methods provide results and data which are surprising, unexpected and contrary thereto. While the utility of this invention is illustrated through the use of several compositions and methods, it will be understood by those skilled in the art that comparable results are obtainable with various other compositions and methods, as are commensurate with the scope of this invention.

Example 1

Cell Culturing

The human cervical carcinoma HeLa cell line (ATCC) is maintained in Dulbecco's Modified Eagle Medium (DMEM) (Gibco) supplement with 10% fetal bovine serum (FBS)(Invitrogen). The human epithelial cell line MCF-10A (TBC) is maintained in DMEM/F12 medium (Gibco) supplement with 10% horse serum (Invitrogen), 20 ng/mL epidermal growth factor (EGF) (Sigma Aldrich), 0.5 mg/mL hydrocortisone (Sigma Aldrich), 100 µg/mL cholera toxins (Sigma Aldrich), and 10 µg/mL insulin (Sigma Aldrich). The cells are cultured at 37° C. with 5% $CO_2$ and plated in T25 flasks (VWR) with aforementioned media.

Example 2

Synthesis of Biocompatible Gold Nanoparticles with Optical Properties in the NIR By adapting a protocol from Xie et at (Xie, J. P. et al., 2007 *Chem Mater* 19, 2823, incorporated herein by reference), gold nanostars (AuNSs) are synthesized by reducing Au(III) chlorate in HEPES buffer to create biocompatible, surfactant-free gold nanoparticles (AuNPs) for in vitro studies. The AuNSs are prepared by mixing 5 µL of 40 mM $HAuCl_4$ (Sigma Aldrich) with 1 mL of 140 mM HEPES buffer. The resonance wavelength of the AuNS is measured using UV-vis spectroscopy. The size of the particles is determined using both high resolution transmission electron microscopy (HR-TEM) and dynamic light scattering (DLS).

To quantify the AuNS concentration, the Au content is measured in a specified volume of AuNS with inductively coupled plasma-mass spectrometry (ICP-MS). Next, by assuming similar numbers of Au atoms in a AuNS and a spherical 30-nm Au particle, the number of AuNS in a specific solution based on the Au content and the number of particles in a similar volume solution of 30-nm Au colloidal particles are estimated. The estimated concentration of the AuNS in the stock solution is 0.2 nM.

Example 3

Loading Aptamer Drugs on the Gold Nanostars

Formation of Apt-AuNS Nanoconstructs

AS-1411 aptamer with a disulfide modification at the 5'-end and a control aptamer (cApt), where all the guanines are replaced with cytosines, are purchased from TriLink Biotechnologies, Inc. HPLC purified aptamers are dissolved in Millipore water (18.2 MΩ-cm) to make 1 mM solutions. The disulfide bond is cleaved by adding 2.5 µL of 25 mM tris(2-carboxyethyl)phosphine (TCEP) (Sigma Aldrich) to 10 µL of the 1 mM aptamer solution. After 30 minutes, the thiolated aptamer solution is added to 10 mL of 0.2 nM solution of AuNS and left overnight to form the nanoconstruct (Apt-AuNS). To increase the surface concentration of aptamers on AuNS (Hill, H. D. et al., 2009 *Acs Nano* 3, 418, incorporated herein by reference), the mixture solution is salted with 2.5 mL of a 500-mM solution of NaCl twice, separated by 4 hours. The size of the nanoconstructs is characterized using DLS.

Calculation of the Numbers of Aptamers Conjugated on AuNS

Cy5-labeled aptamer is used to estimate the number of aptamers functionalized on a single AuNS. The Cy5 is placed at the 3'-end of the aptamer, while the 5'-end is attached to the AuNS surface via the gold-sulfur bond. To estimate the amount of aptamers involved in the AuNS functionalization, fluorescence S3 measurements of the free Cy5-labeled aptamers are taken in the solution before the conjugation. Cy5-labeled aptamers are then conjugated on AuNS based on protocol discussed above. After 24 hours, the nanoconstruct solution is centrifuged at 15,000 rpm for 11 minutes and the supernatant is collected. The fluorescence of the supernatant is measured to determine the amount of aptamers which did not react with the AuNS. Based upon these results, approximately 950G-quartet homodimer aptamers functionalized on a single AuNS are found.

Example 4

Establishing Targeting Capabilities of Apt-AuNS to the Cell Nucleus

Fluorescence Imaging of Apt-AuNS Inside Cells

HeLa cells ($2 \times 10^4$ cells/coverslip) are plated on poly-L-Lysine treated coverslips and maintained with DMEM with 10% fetal bovine serum (FBS). After cell growth (37° C. in 5% $CO_2$) for 24 hours, the growth medium is removed, and the cells are washed 3 times with phosphate buffered saline (PBS) (Invitrogen). 300 μL of 0.3 nM 3' labeled Cy5-Apt-AuNS in DMEM are added to cells for different incubation times (2.5, 5, 7, and 24 hours). For control, 0.3 nM of non-targeting 3' labeled Cy5-cApt-AuNS is added to HeLa cells for similar incubation times. After the NP solutions are removed, the cells are washed 3 times with PBS. 200 μL of 4% paraformaldehyde (Sigma Aldrich) is added for 20 minutes to fix the cells, followed by washing the samples 3 times with PBS. A drop of ProLong Gold antifade reagent with DAPI (Invitrogen) is added to each well, and then the sample is mounted on a glass slide for fluorescence imaging.

Transmission Electron Microscopy (TEM) Imaging of Apt-AuNS Inside Cells

TEM imaging (JEOL 1230 TEM, 80.0 kV) is performed to complement the confocal fluorescence results. HeLa cells are plated at $2 \times 10^5$ cells per well in a 12-well plate for 24 hours. After removal of the growth media, 3 mL of the 0.3 nM Apt-AuNS in DMEM is added to each well for 2-, 5-, 7- and 24-hour incubation. HeLa cells are harvested by treating with 0.25% trypsin-EDTA for 5 minutes at 37° C. in 5% $CO_2$. The cells are then centrifuged at 500×g for 5 minutes. The supernatant is removed, and the pellets resuspended and washed in PBS.

The cells are fixed by the first infiltration step using a Pelco Biowave microwave. Two exchanges of the primary fixative are made using 2% paraformaldehyde and 2.5% glutaraldehyde in a 0.05M sodium phosphate buffer followed by two buffer washes. The secondary fixative of 1.5% osmium tetroxide in distilled (DI)-water is followed by 2 DI-water rinses. Acetone is used for the dehydration series and infiltration steps. The EMBed 812 resin is made to medium hardness. Bench infiltration steps at room temperature include resin to acetone ratios of 1:1 for 4 hours and 2:1 overnight, followed by 100% resin for 3 hours, and 100% resin for another hour. Polymerization takes place in a 60° C. oven for 24 hours, and no additional staining is done. A Leica Ultracut S or RMC MT-6000 XL microtome is used to collect 90-nm thick sections.

Example 5

Determining the Amount of Aptamer Release from AuNS Upon NIR Irradiation

Laser Experiment Setup

The femtosecond NIR pulses used in the irradiation experiments are generated using a 1-kHz Ti:sapphire regenerative amplifier (Spitfire Pro, Spectra-Physics) seeded by a Ti:sapphire oscillator (Tsunami, Spectra-Physics). The center wavelength is set to 800 nm, and the pulse duration is 40-50 fs. The beam is focused to a 4.5-mm diameter spot at the sample using a 50-cm focal length plano-convex lens. The average pump power is attenuated to 760 mW, corresponding to a power density of 4.8 W/cm$^2$, using a gradient neutral density filter wheel. Samples are irradiated in the 96-well plates, and the irradiation time is controlled to within 2 milliseconds by a shutter (Uniblitz, Vincent Associates) connected to a computer.

Release of Aptamer from Nanoconstructs in PBS Buffer

80 μL of 0.2 nM Apt-Cy5-AuNS is added in each of a 96-wells plate. The Cy5 dye is located at the 5' end of aptamer which also contains thiolated group attaching to the AuNS. Because the dye is closest to the surface of the particle (<1 nm), the fluorescence is expected to quench by the gold (Anger, P. et al., 2006 Phys Rev Lett 96, 113002, incorporated herein by reference). Each well is irradiated (hv) for 2 seconds using a 40 femtosecond (fs), 1 kHz repetition rate, 800-nm pulsed laser at S5 different power densities (from 0.5 W/cm$^2$ to 4.8 W/cm2), and the fluorescence is measured using a PC1 fluorimeter. Fluorescence intensity of the solution is determined with all the thiolated Cy5-labeled aptamer replaced from AuNS with mercaptobutanol in order to calculate the percentage of released aptamer from fs-irradiation (Demers, L. M. et al., 2000 Analytical Chemistry 72, 5535, incorporated herein by reference. Results show that approximately 20% of the DNA is released from the AuNSs after fs-irradiation at 4.8 W/cm$^2$ for 2 seconds.

Release of Aptamer from Nanoconstructs in Cells

To monitor Apt release from nanoconstructs in the cells, HeLa cells are used plated at $10 \times 10^3$ per well in 48 wells of a 96-well plate for 24 hours. After removal of the growth media from the wells, 100 μL of 0.3 nM Apt-Cy5-AuNS in RPMI-1640 colorless media is added to each well and incubated for 7 hours. Half of the wells are subjected to 2-second irradiation at 4.8 W/cm$^2$ (same conditions as in buffer), while the other half are untreated to serve as a control. Apt-AuNS HeLa cells are then collected by trypsinization (5 min) of the cells from the plate and spun down (350×g) for 5 minutes to form a cell pellet. The pellets are resuspended and washed twice in PBS, after which PBS is removed and replaced with Binding buffer (Invitrogen). The fluorescence signal measured by flow cytometry shows an increase by 2 times in fs-irradiated cells.

Example 6

Determining γ-H2AX Protein Binding to Assess dsDNA Breaks in the Cell Nucleus

Double-stranded DNA breaks (DSBs) are determined by immunostaining of Serine-139 phosphorylated γ-H2AX protein with the primary antibody anti-γ-H2AX (Sigma Aldrich) (Rogakou, E. P. et al., 1998 J Biol Chem 273, 5858, incorporated herein by reference). The secondary antibody, goat-anti-mouse IgG labeled with the green fluorescent dye FITC (Millipore), is attached to the primary antibody. dsDNA breaks are indicated by the bright green FITC signals. HeLa cells ($2 \times 10^4$ cells/coverslip) are plated on poly-L-Lysine treated coverslips. After treatment, the cells are fixed with 4% paraformaldehyde for 20 minutes. The fixed cells are then incubated with 1 mL of PBS for 5 minutes and then treated with 300 μL of PBS containing 0.5% Triton X-100 (Invitrogen) for 3 minutes to enhance permeability. The cells are washed with PBS 3 times and incubated with primary antibody anti-γ-H2AX diluted in 1% Tween-PBS (T-PBS) solution containing 0.1% BSA (1:100) for one hour.

The cells are then washed with PBS 3 times and incubated with secondary antibody diluted in T-PBS (1:250) for 20 minutes. A drop of ProLong Gold antifade reagent with DAPI (Invitrogen) is added to the coverslip, and the sample is then placed on a glass slide for confocal fluorescence imaging.

Figure 12:
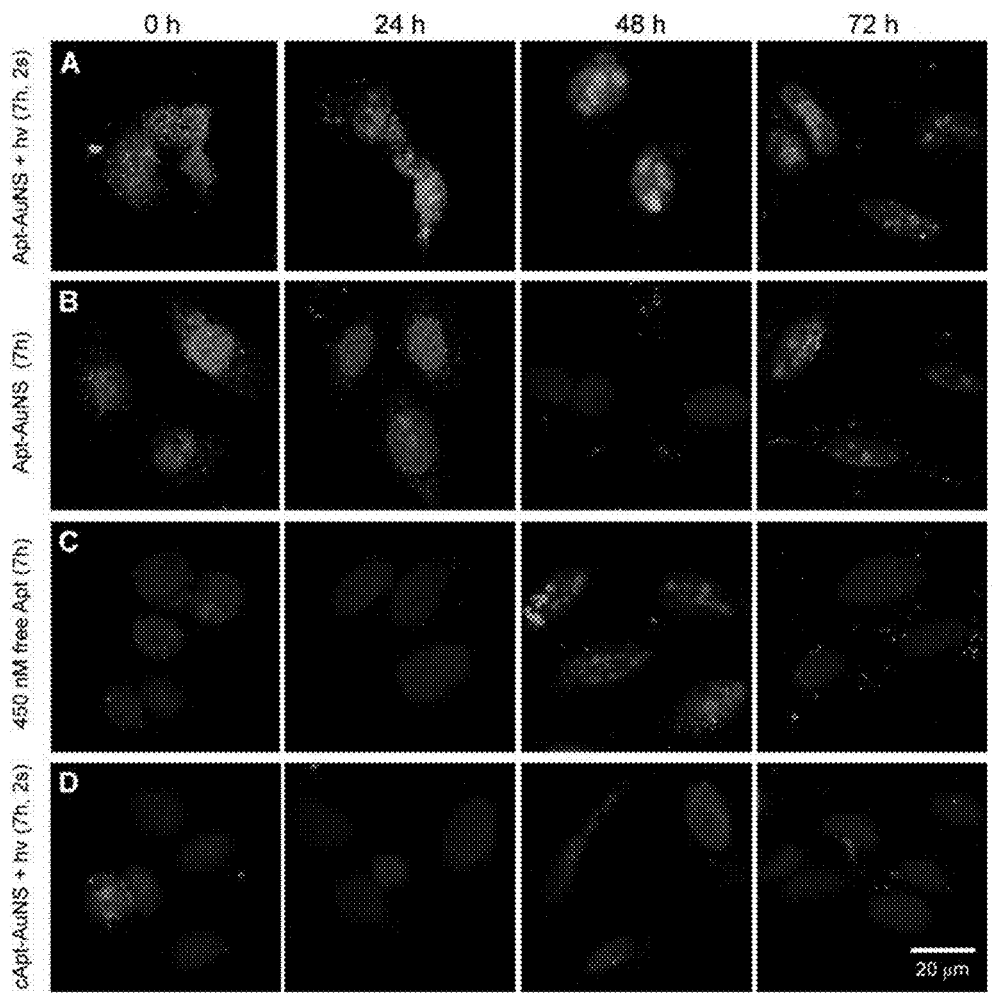
FIG. 12 Confocal fluorescence microscopy of double stranded DNA (A) Apt-AuNS+hv (7 h, 2 s); (B) Apt-AuNS (7 h); (C) 450 nM free Apt (7 h); and (D) cApt-AuNSs+hv (7 h, 2 s).

FIGS. 12A-D show these confocal fluorescence images. DSBs occur in the nuclei of cancer cells treated with Apt-AuNSs, as depicted in FIG. 12A for Apt-AuNSs+hv (7 h, 2 s), FIG. 12B for Apt-AuNSs (7 hours) and FIG. 12C for 450 nM free Apt (7 hours). Among these conditions, the highest quantity of DSBs foci are observed in the nuclei of cells treated with Apt-AuNSs for 7 hours followed by irradiation (with the same conditions) of Apt-AuNSs+hv (7 h, 2 s). Although DSBs are found in HeLa cells after treatment with free aptamers at concentration similar to that of aptamers conjugated to the AuNS (450 nM, 7 h), the quantity of DSBs foci is significantly less than those of cells treated with Apt-AuNSs+hv. FIG. 12D shows that only negligible amount of DSBs are observed on cells when they are treated with cApt-AuNSs+hv (7 h, 2 s).

Example 7

Determining Apoptosis in Cancer Cells Treated with Nanoconstructs

Apo-ONE Homogeneous Caspase-3/7 Assay Kit (Promega) is used to test caspase 3/7 activity, apoptotic indicators, in cancer cells after light-triggered release of the Apt. The assay is performed following the protocol by Promega (Promega, in *Technical Bulletin* P. Corporation, Ed. (Promega Corporation, Madison, Wis., 2009), pp. 8). The cells are plated on a 96-wells plate (~10,000 cells/well) for 24 hours. After treatment, the cells are lysed with the mixture, which contains pro-fluorescence substrate (Z-DEVD-R110) and bifunctional cell lysis/activity buffers. The caspase 3/7 activity is measured using Synergy 3 micro-plate reader (NU-HTA) to determine the fluorescence intensity of R110 ($487_{ex}/528_{em}$ nm) at different time points (0, 24, 48, and 72 hours) after release of the aptamer. Error bars are calculated by taking the ratio between standard deviation of the sample set and square root of the sample population (N=18). Two-way ANOVA is performed (Origin $8^{th}$ ed.) to evaluate significant differences between the factor level means within a factor and for interactions between the factors of different sample sets.

Figure 13:
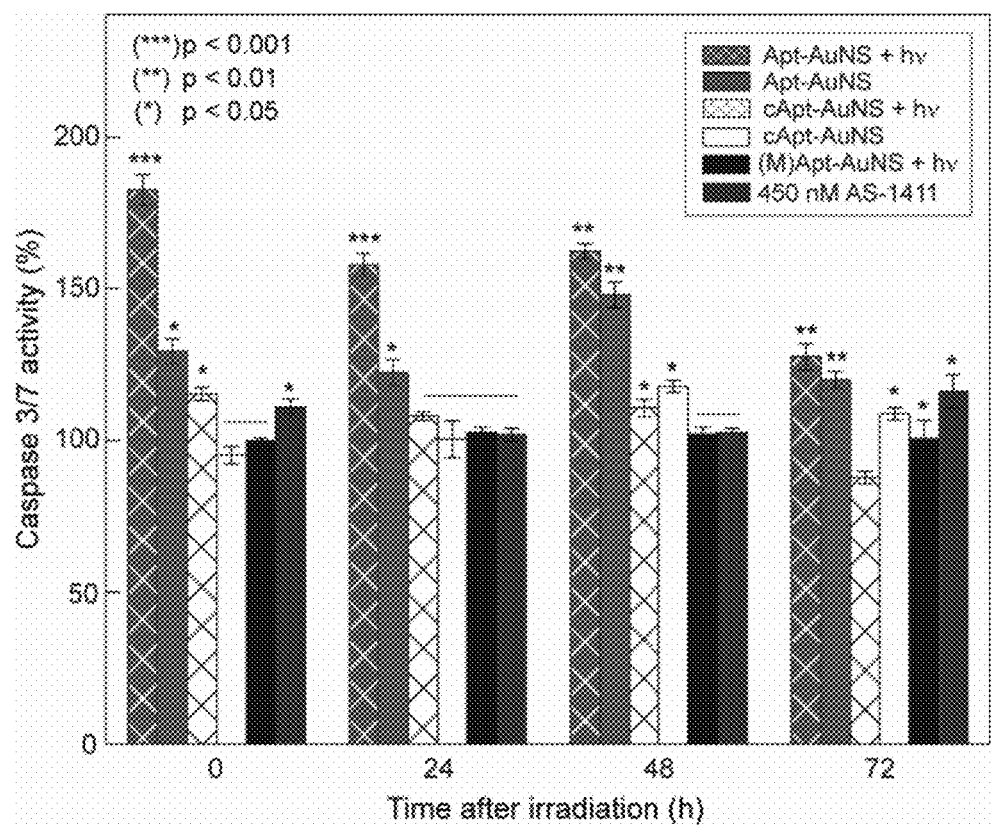
FIG. 13 is a graph showing caspase 3 and 7 activities of HeLa cells treated with Apt-AuNS under various conditions over 72 hours.

FIG. 13 is a graph showing caspase 3 and 7 activities of HeLA cells treated with Apt-AuNS under various conditions over 72 hours. Increases in the caspase activities are observed over the 72 hours, regardless of whether the aptamer is released from the nanoparticles. The caspase activity is highest in samples treated with Apt-AuNSs+hv. Surprisingly, the caspase activity of cells treated with 450 nM of free aptamer (a concentration similar to that estimated by the number of aptamers on the AuNSs and the concentration of AuNS) is much lower than those treated with Apt-AuNSs. The caspase activities of HeLa cells treated with cApt-AuNSs are not noticeable even after laser irradiation to release cApt. In addition, the caspase activity of MCF-10A cells treated with Apt-AuNSs does not increase after laser irradiation. In FIG. 13, lines over bars indicate groups that are not significantly different.

Example 8

Evaluating Cell Viability of Cell Populations

Cell-Titer Blue Cell Viability Assay (Promega) is used to determine the viability of cells. This kit contains highly purified non-fluorescent rezasurin in buffer. Viable cells reduce rezasurin to resofurin, which is a highly fluorescent molecule. Non-viable cells, however, lose their metabolic activity and do not reduce rezasurin. Cells are plated on a 96-wellplate (~10,000 cells/well) for 24 hours. After treatment, cell viability is determined by measuring the fluorescence intensity ($560_{ex}/590_{em}$ nm) of resofurin at different time points (0, 24, 48, and 72 hours). Error bars are calculated by taking the ratio between standard deviation of the sample set and square root of the sample population (N=18). Two-way ANOVA is performed (Origin $8^{th}$ ed.) to evaluate significant differences between the factor level means within a factor and for interactions between the factors of different sample sets.

Figure 14:
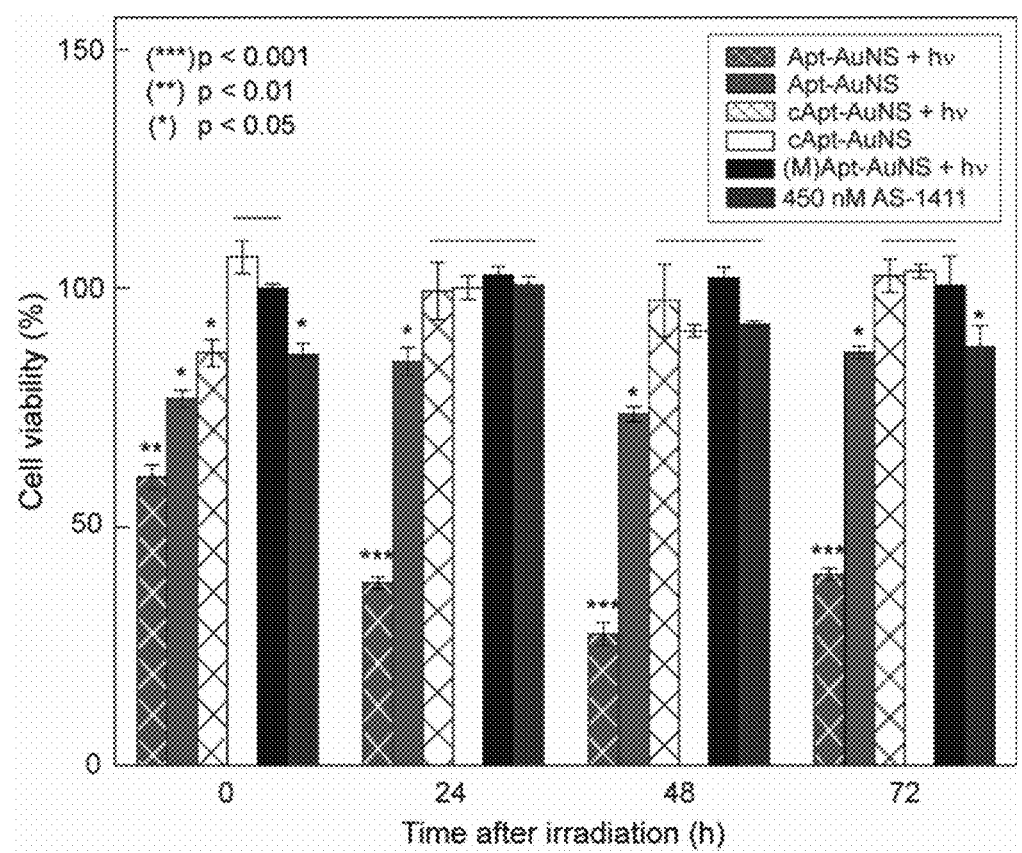
FIG. 14 is a graph showing cell viability assay on HeLa cells treated with Apt-AuNS under various conditions over 72 hours.

FIG. 14 is a graph showing the cell viability assay on cells treated under various conditions. HeLa cells treated with Apt-AuNS show decreased cell viability over 72 hours. Consistent with increased amounts of NE folding, the HeLa cell population treated with Apt-AuNSs+hv decreases over 70% between 48 and 72 hours after release of the aptamer, which is much higher than that of Apt-AuNS only treated cells (ca. 25%). Similar to the trend observed in caspase activity (FIG. 13), the viability changes of free aptamer (450 nM) treated HeLa cells is minimal (ca. 100%). The viabilities of cApt-AuNS treated HeLa cells do not decrease regardless of laser irradiation. Similarly, the viability of Apt-AuNS treated MCF-10A cells after light-irradiation is nearly 100%. Again, in FIG. 14, lines over bars indicate groups that are not significantly different.

In summary, direct visualization of the interaction between a drug-loaded nanoconstruct and a cancer cell nucleus is achieved, and correlating the resulting morphological deformations in the NE with increased therapeutic efficacy is made possible. By taking advantage of the shuttling protein nucleolin over-expressed on the cancer cell surface, the nanoconstruct is delivered near the nucleus. This nanoscale proximity of the nanoconstruct results in extreme deformation and invagination of the NE localized at the site of the construct. These morphology changes are exacerbated upon ultra-fast, light-triggered release of the aptamer from the nanostar. Moreover, these changes found in the NE structure are strongly correlated with important biological responses in cancer cells, including increased apoptosis and decreased cell viability.

Although the invention has been described in detail for the purposes of illustration, it is understood that such detail is solely for that purpose, and variations can be made therein by those skilled in the art without departing from the spirit and scope of the invention as defined in the claims that follow.

What is claimed:

1. A method of inducing changes to a nuclear phenotype of a cell comprising
   providing a nanoconstruct comprising an aptamer and a gold nanostar;
   administering the nanoconstruct to a cellular medium;
   incubating the medium with the nanoconstruct for a time greater than 2.5 hours;
   exciting the nanoconstruct with a femtosecond pulse laser; and
   releasing the aptamer from the gold nanostar into the nucleus of a cell in the medium to afford invaginations in nuclear membrane, thereby inducing changes to the nuclear phenotype.

2. A method according to claim 1 wherein the aptamer is AS-1411.

3. A method according to claim 1 wherein the cell is a cancer cell.

4. A method according to claim 1 wherein the nanoconstruct is transported to the nucleus of the cell by binding to nucleolin to form a complex, the complex internalized by the cell.

5. A method according to claim 1 wherein the invaginations lead to an increase in caspase activity.

6. A method according to claim 5 wherein the caspase is selected from the group of caspase 3, caspase 7 and both caspase 3 and caspase 7.

7. A method according to claim 6 wherein the increase in caspase activity induces cell apoptosis.

8. A method according to claim 7 wherein the cell is a cancer cell.

9. A method according to claim 1 wherein the invaginations in nuclear membrane lead to decreased cell viability.

10. A method according to claim 9 wherein the cell is a human cervical carcinoma cell.

11. A two-component nanoconstruct comprising an AS-1411 homodimer aptamer and a gold nanostar, wherein the gold nanostar supports about 950 AS-1411 homodimer aptamers.

12. A method of inducing changes to a nuclear phenotype of a cell, comprising:
providing a nanoconstruct of claim 11;
administering the nanoconstruct to a cellular medium comprising carcinoma cells;
incubating the medium with the nanoconstruct for a time sufficient for transport of the nanoconstruct to the nucleus of a carcinoma cell;
irradiating the nanoconstruct with a femtosecond pulse laser to release the aptamers from the gold nanostar into the nucleus of a carcinoma cell, thereby inducing changes to the nuclear phenotype.

13. A method for treating a hyperproliferative cell disorder in an individual comprising administering to the individual in need thereof a nanoconstruct comprising an aptamer and a gold nanostar, the nanoconstruct administered in an amount effective to reduce proliferation of one or more cells; incubating the nanoconstruct for a time greater than 2.5 hours; and irradiating the nanoconstruct with a femtosecond pulse laser after transport of the nanoconstruct to the nucleus of one or more cells, whereby the aptamer of the nanoconstruct induces apoptosis of the one or more cells.

14. A method according to claim 13 wherein the aptamer is capable of binding to nucleolin.

15. A method according to claim 13, wherein the nanoconstruct binds to nucleolin.

16. A method according to claim 15, wherein binding of the nanoconstruct to the nucleolin forms a complex and mediates internalization of the complex in a cell.

17. A method according to claim 16, wherein the cell is a cancer cell.

18. A two-component nanoconstruct according to claim 11, wherein the AS-1411 homodimer aptamer is modified with thiol groups.

19. A two-component nanoconstruct comprising a gold nanostar and a AS-1411 homodimer aptamer modified with thiol groups, the nanostar supporting about 950 AS-1411 thiol-modified homodimer aptamers.

20. A method for treating a hyperproliferative cell disorder in an individual comprising administering to the individual in need thereof a nanoconstruct comprising a thiolated aptamer on a gold nanostar, the nanoconstruct administered in an amount effective to reduce proliferation of one or more cells; incubating the nanoconstruct for a time greater than 2.5 hours; and irradiating the nanoconstruct with a femtosecond pulse laser after transport of the nanoconstruct to the nucleus of one or more cells, whereby the aptamer of the nanoconstruct induces apoptosis of the one or more cells.

21. A method according to claim 20, wherein the nanoconstruct binds to nucleolin to form a complex and mediates internalization of the complex in a cell.

22. A method according to claim 21, wherein the cell is a cancer cell.

* * * * *